(12) United States Patent
Albertazzi

(10) Patent No.: US 9,931,199 B2
(45) Date of Patent: Apr. 3, 2018

(54) METHODS AND APPARATUS FOR TREATING KERATOCONUS

(71) Applicant: Roberto Gustavo Albertazzi, Buenos Aires (AR)

(72) Inventor: Roberto Gustavo Albertazzi, Buenos Aires (AR)

( * ) Notice: Subject to any disclaimer, the term of this patent is extended or adjusted under 35 U.S.C. 154(b) by 323 days.

(21) Appl. No.: 14/704,931

(22) Filed: May 5, 2015

(65) Prior Publication Data
US 2016/0038276 A1 Feb. 11, 2016

Related U.S. Application Data

(60) Provisional application No. 61/988,878, filed on May 5, 2014.

(51) Int. Cl.
*A61F 2/14* (2006.01)
*A61B 3/107* (2006.01)
*A61B 3/00* (2006.01)
*A61F 9/007* (2006.01)

(52) U.S. Cl.
CPC ............ *A61F 2/147* (2013.01); *A61B 3/0025* (2013.01); *A61B 3/0033* (2013.01); *A61B 3/0058* (2013.01); *A61B 3/107* (2013.01); *A61F 9/007* (2013.01)

(58) Field of Classification Search
CPC ..................................................... A61F 2/147
USPC ....................................................... 715/771
See application file for complete search history.

(56) References Cited

U.S. PATENT DOCUMENTS

| 6,444,791 | B1 * | 9/2002 | Quay | A61K 38/55 424/450 |
|---|---|---|---|---|
| 9,526,581 | B2 * | 12/2016 | Bodduluri | A61B 17/32053 |
| 9,788,996 | B2 * | 10/2017 | Roy | A61F 9/0026 |
| 2005/0071002 | A1 * | 3/2005 | Glazier | A61F 2/1613 623/6.13 |
| 2005/0119739 | A1 * | 6/2005 | Glazier | A61F 2/1613 623/6.13 |

(Continued)

OTHER PUBLICATIONS

Nomogram App on Google Play, available at https://play.google.com/store/apps/details?id=com.ajlsa.nomograma, Mar. 13, 2015.

*Primary Examiner* — Reza Nabi
(74) *Attorney, Agent, or Firm* — Harness, Dickey & Pierce, P.L.C.

(57) ABSTRACT

A method of treating keratoconus in an eye of a patient includes measuring a surface of a cornea of the eye to acquire eye topography data. The method includes, based on the eye topography data, selecting a topographic pattern from topographic patterns displayed in a graphical user interface. The method includes entering vision corrective parameters for the eye of the patient into the graphical user interface. The method includes actuating a processing module to obtain a surgical plan based on the selected topographic pattern and the entered vision corrective parameters. The method includes reviewing intrastromal corneal ring segment (ICRS) implantation surgery parameters specified by the surgical plan and displayed in the user interface. The ICRS implantation surgery parameters include specification of at least one ICRS. The method includes performing implantation surgery of the at least one ICRS into the eye of the patient according to the surgical plan.

27 Claims, 24 Drawing Sheets

(56) References Cited

U.S. PATENT DOCUMENTS

| | | | | |
|---|---|---|---|---|
| 2005/0134799 A1* | 6/2005 | Thompson | A61F 9/007 | 351/222 |
| 2008/0181893 A1* | 7/2008 | Lobov | A61K 38/1709 | 424/135.1 |
| 2009/0247999 A1* | 10/2009 | Tuan | A61F 9/008 | 606/5 |
| 2010/0256965 A1* | 10/2010 | Rathjen | A61F 9/00831 | 703/11 |
| 2011/0065642 A1* | 3/2011 | Mashima | A61K 38/38 | 514/15.2 |
| 2011/0125451 A1* | 5/2011 | Cheifetz | F24J 3/08 | 702/130 |
| 2011/0152219 A1* | 6/2011 | Stagni | A61K 9/0048 | 514/81 |
| 2011/0190742 A1* | 8/2011 | Anisimov | A61F 9/0079 | 606/5 |
| 2011/0268170 A1* | 11/2011 | Masuhara | G01R 31/31709 | 375/228 |
| 2012/0121567 A1* | 5/2012 | Troisi | A61K 31/203 | 424/94.1 |
| 2012/0229767 A1* | 9/2012 | Alpins | A61B 3/0025 | 351/212 |
| 2013/0178821 A1* | 7/2013 | Foschini | A61K 31/525 | 604/501 |
| 2013/0190736 A1* | 7/2013 | Fabrikant | A61F 9/00806 | 606/5 |
| 2013/0261503 A1* | 10/2013 | Sherman | A61F 2/4657 | 600/587 |
| 2013/0267528 A1* | 10/2013 | Pinelli | A61K 9/0048 | 514/251 |
| 2013/0310732 A1* | 11/2013 | Foschini | A61K 9/0009 | 604/20 |
| 2014/0303173 A1* | 10/2014 | Foschini | A61K 9/0009 | 514/251 |
| 2016/0038276 A1* | 2/2016 | Albertazzi | A61F 9/007 | 623/5.12 |
| 2016/0143777 A1* | 5/2016 | Roy | A61F 9/013 | 604/20 |
| 2016/0175153 A1* | 6/2016 | Krumeich | A61F 9/00825 | 606/5 |
| 2016/0302971 A1* | 10/2016 | Morley | A61F 9/00825 | |
| 2017/0173262 A1* | 6/2017 | Veltz | A61M 5/1723 | |

* cited by examiner

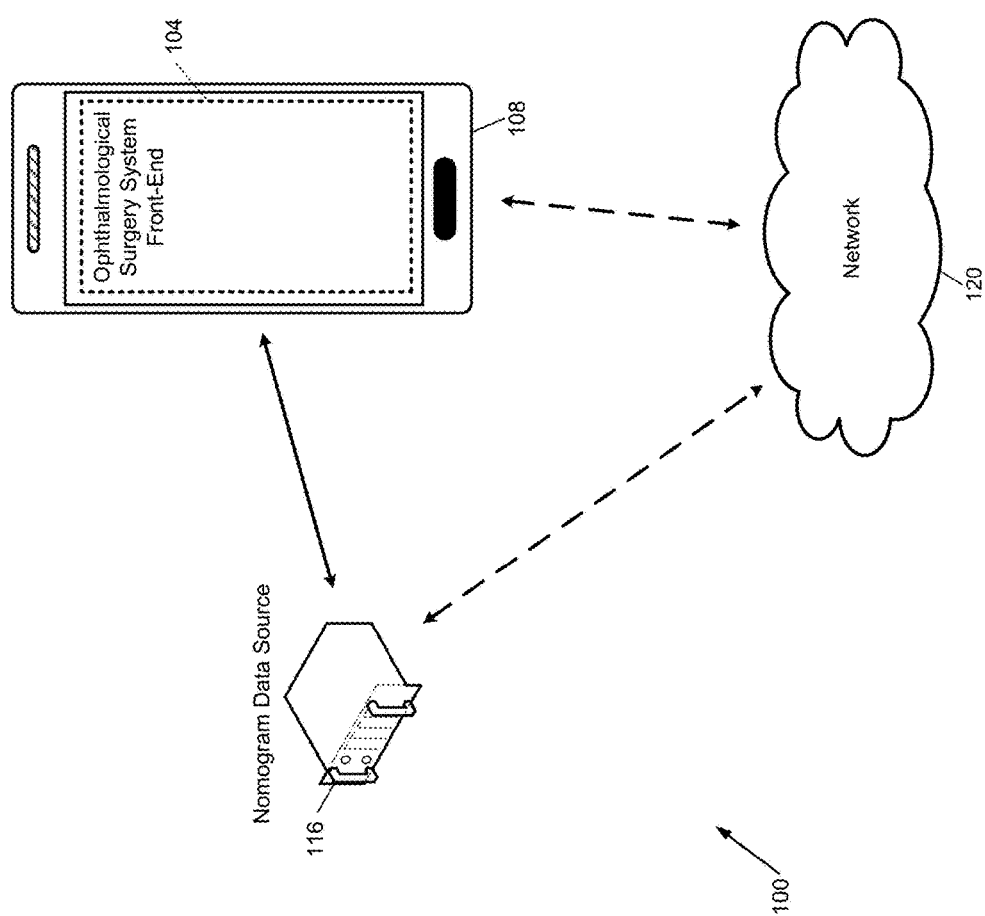

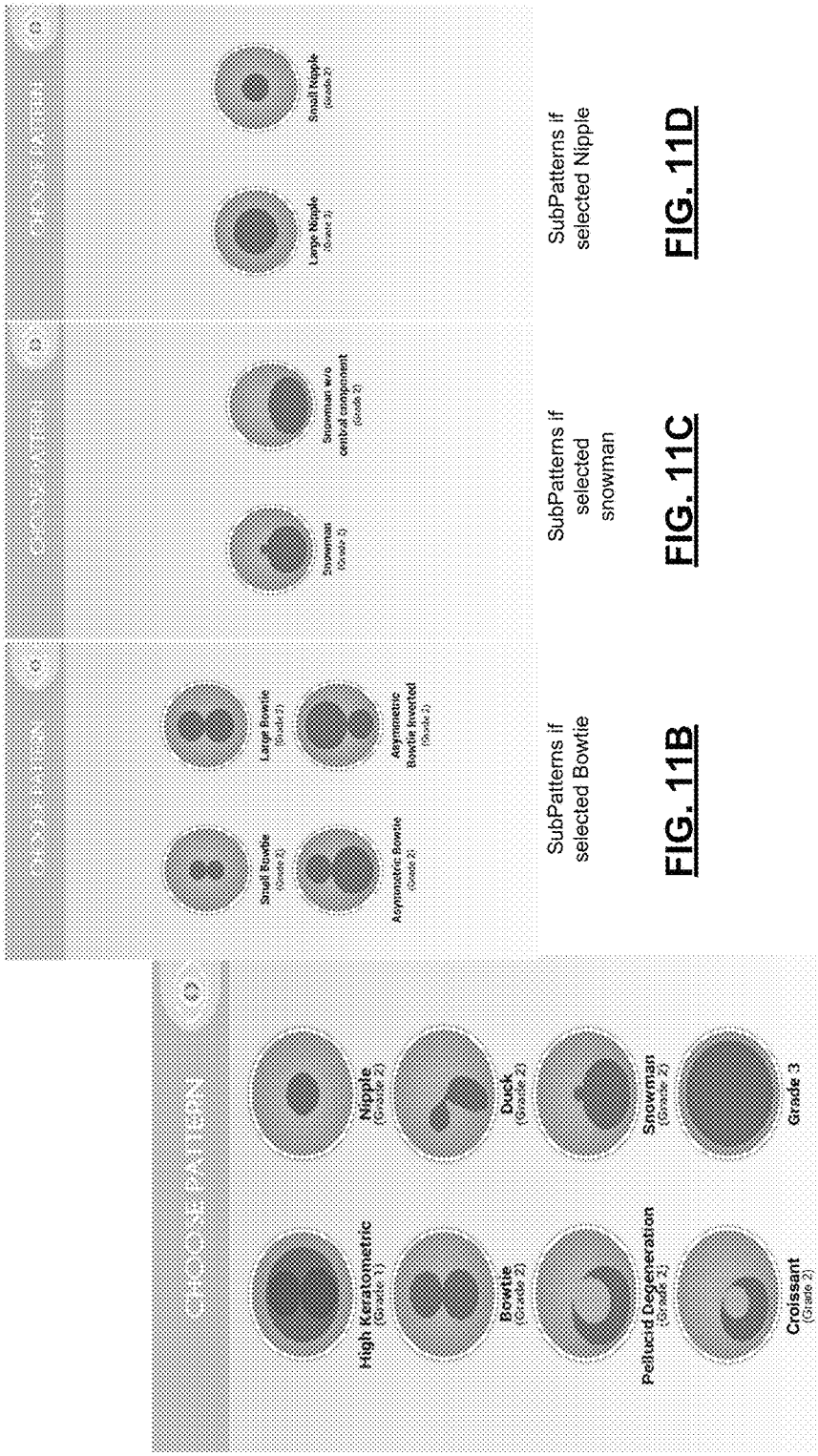

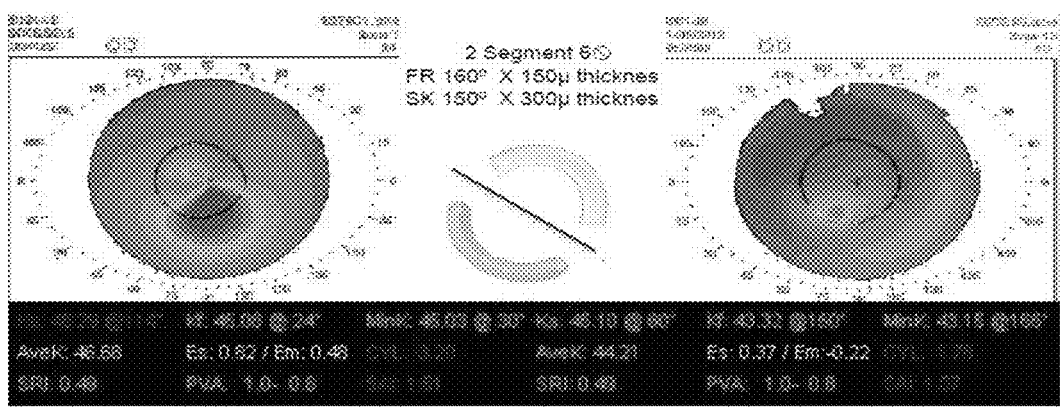
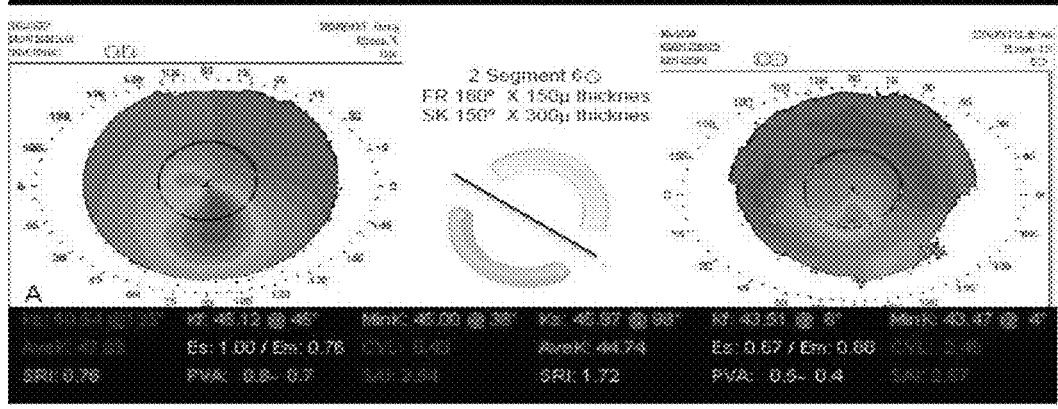
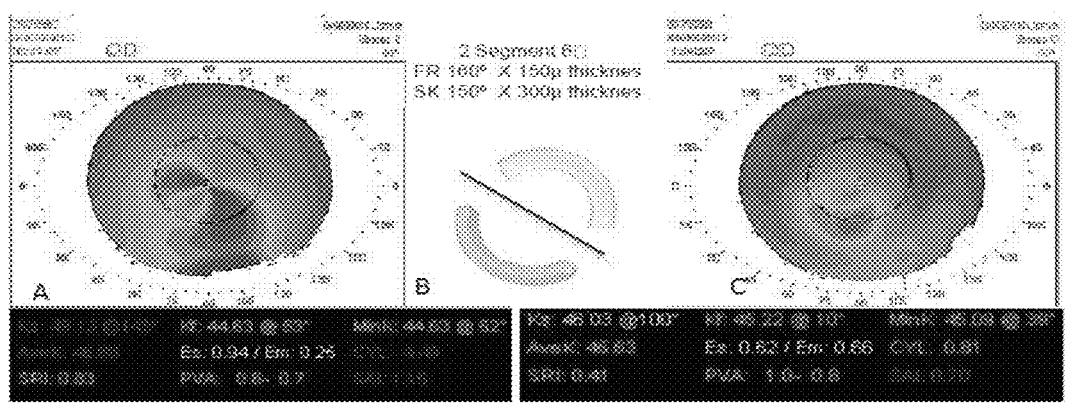
FIG. 21B

METHODS AND APPARATUS FOR TREATING KERATOCONUS

CROSS-REFERENCE TO RELATED APPLICATION

This application claims the benefit of U.S. Provisional Application No. 61/988,878, filed on May 5, 2014. The entire disclosure of the application referenced above is incorporated herein by reference.

FIELD

The present disclosure generally relates to surgically treating disorders of the eye and more particularly to surgical treatment of keratoconus using intrastromal corneal ring segments.

BACKGROUND

Keratoconus is a chronic progressive noninflammatory disorder in which the cornea assumes a conical shape. The corneal thinning induces irregular astigmatism, myopia, and ectasia, leading to a mild to severe decrease in vision quality. It is one of the most common corneal diseases, with a prevalence of 54 in 100,000 and an annual incidence in the general population of 2 in 100,000. Many options for the management of this pathological condition have been described, including corneal collagen crosslinking, fitting a rigid gas-permeable (RGP) contact lens, intrastromal corneal ring segment (ICRS, also known as an intracorneal ring segment) implantation, and lamellar or penetrating keratoplasty.

ICRSs may be implanted through a small surgical incision on the perimeter of the cornea and were originally developed to correct myopia. Several studies report the effectiveness of this surgical technique for improving visual acuity and reducing the refractive error and the mean keratometry (K) value in cases of keratoconus. ICRS implantation may be an effective method to regularize the corneal shape, reducing astigmatism in patients with a clear cornea and contact lens intolerance. The visual and refractive outcomes of this surgery may be highly dependent on the stage of keratoconus.

From a biomechanical viewpoint, the corneal tissue is considered a viscoelastic material that can be modified in response to the presence of a force such as intraocular pressure. In some cases, alterations inside the biomechanical structure found with keratoconus lead to progression of the disease, which has been shown to be more severe during the second and third decades of life. In addition to the benefit of corneal remodeling and improvement in the optical quality of the cornea, some long-term studies report that ICRS implantation may halt the progression of keratoconus.

The background description is provided for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

SUMMARY

A method of treating keratoconus in an eye of a patient includes measuring a surface of a cornea of the eye to acquire eye topography data. The method includes, based on the eye topography data, selecting a topographic pattern from topographic patterns displayed in a graphical user interface. The method includes entering vision corrective parameters for the eye of the patient into the graphical user interface. The method includes actuating a processing module to obtain a surgical plan based on the selected topographic pattern and the entered vision corrective parameters. The method includes reviewing intrastromal corneal ring segment (ICRS) implantation surgery parameters specified by the surgical plan and displayed in the user interface. The ICRS implantation surgery parameters include specification of at least one ICRS. The method includes performing implantation surgery of the at least one ICRS into the eye of the patient according to the surgical plan.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 1A is a diagram of an example smartphone implementation of a system for treating keratoconus according to the principles of the present disclosure.

FIGS. 11A-11D are screenshots of an example graphical user interface showing representative patterns and sub-patterns for corneal topography.

FIGS. 21A-21B are comparisons of pre-operation and post-operation corneal measurements for a first group of patients and a second group of patients, respectively.

In the drawings, reference numbers may be reused to identify similar and/or identical elements.

DETAILED DESCRIPTION

Several nomograms for intrastromal corneal ring segment (ICRS) implantation in keratoconus have been developed for planning surgical intervention. However, it has traditionally been difficult to summarize and apply such nomograms as they may vary depending on manufacturer indications, type of ring selected, and corneal ectasia pattern. The present disclosure presents a set of nomograms for a variety of different patient characteristics and describes a system and method for planning and surgically treating keratoconus. The present disclosure may allow for more intuitive and accurate surgical planning, leading to enhanced surgical outcomes, which may be measured by tectonic and refractive results.

Figure 1B:
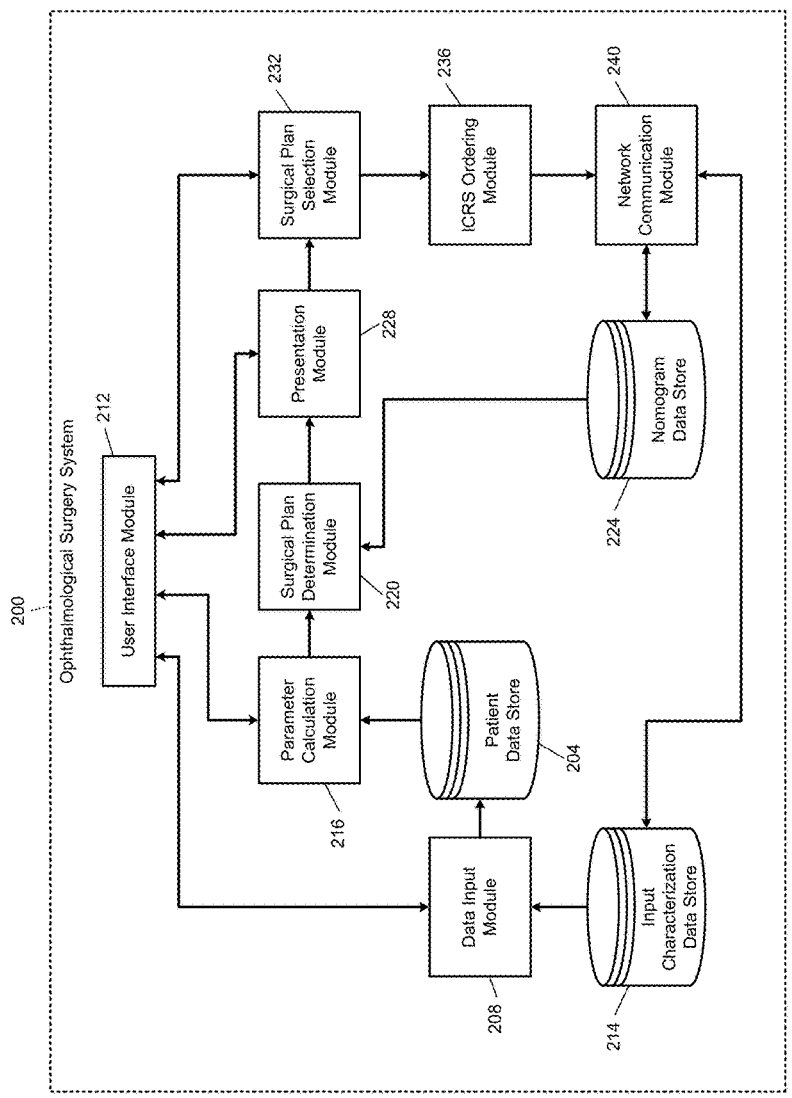
FIG. 1B is a block diagram of an ophthalmological surgery system for treating keratoconus.

FIG. 1A is a diagram of an example implementation of a system 100 for determining a surgical plan for treating keratoconus in a cornea of an eye of a patient, and the like. In the system 100, an ophthalmological surgery system front-end 104 operates on a user device 108, which may be a portable device such as a tablet or smartphone. The ophthalmological surgery system front-end 104 may take the form of a native application downloaded to the user device 108 or a web-based system accessed using a web browser installed on the client device 108.

The ophthalmological surgery system front-end 104 may prompt the user for patient data as described in more detail below, calculate surgical parameters based on the entered patient data, and present one or more surgical plan options to the user. The ophthalmological surgery system front-end 104 may rely on nomograms that specify surgical parameters and surgical plans according to the entered patient data. These nomograms may be provided by a nomogram data source 116.

The nomograms from the nomogram data source 116 may be provided on demand to the ophthalmological surgery system front end 104. The ophthalmological surgery system front end 104 may alternatively or additionally store nomograms from the nomogram data source 116 fixed at a certain point in time, such as when the ophthalmological surgery system front end 104 is compiled or packaged.

Updates to nomograms stored in the nomogram data source 116 may be retrieved periodically from the nomogram data source 116 and/or based on an update notification sent to the ophthalmological surgery system front end 104. The ophthalmological surgery system front end 104 may communicate with the nomogram data source 116 via a network 120, which may be a distributed wide area network such as the internet, or may be a local area network. The nomogram data source 116 may be operated and updated by a provider of the ophthalmological surgery system front end 104. In other implementations, the nomogram data source 116 may be operated by a third party, and there may be a variety of choices of nomogram data sources (including the nomogram data source 116). The developer of the ophthalmological surgery system front end 104 may operate one or more of these nomogram data sources. Other nomogram data sources may be maintained and operated by organizations such as professional ophthalmological organizations and companies such as manufacturers and distributors of ICRSs.

The ophthalmological surgery system front end 104 uses patient data provided by the user and, in some implementations, also calculations based on the provided data, to select one or more nomograms to recommend for treatment of a patient. The ophthalmological surgery system front end 104 may allow the user to select one of the treatment plans and may allow for the user to order the specified ICRSs from a distributor or manufacturer (not shown) via the network 120. A surgeon, who may also act as the user of the ophthalmological surgery system front end 104, may perform a surgical procedure on the patient based on parameters, such as incision access (described in more detail below) as displayed by the ophthalmological surgery system front end 104.

A functional block diagram of an example implementation of an ophthalmological surgery system 200 is shown. A patient data store 204 stores data relating to the eye or eyes of a patient. The patient may be identified by a numerical identifier so that a separate mapping is required to tie the patient data in the patient data store 204 to a specific individual. Alternatively, identifying information such as name and age may be included in the patient data store 204.

In either case, the patient data store 204 may be encrypted to prevent unauthorized access to the data. In various implementations, each patient's data in the patient data store 204 may be separately encrypted, so that unencrypted data in a memory system of the ophthalmological surgery system 200 does not contain the entire contents of the patient data store 204 at any one time. The patient data store 204 instead may be stored in persistent storage, such as a flash-based or magnetic hard disk drive.

The patient data store 204 may receive patient data from the data input module 208, which checks and sanitizes data received via a user interface module 212. The user interface module 212 may be implemented as shown in FIG. 1A by the ophthalmological surgery system front end 104. The user interface module 212 may include graphical displays, audio outputs, mouse, pen, and keyboard inputs, and/or combined input/output devices, such as a touchscreen.

The data input module 208 may perform bounds checking and identify inputs that are not within expected ranges and combinations of inputs that are considered invalid. Validated and sanitized data is stored in the patient data store 204.

An input characterization data store 214 may specify to the data input module 208 which parameters should be entered for a patient. These parameters may include, for example, a general shape of asphericity of the eye, pachymetry (which may be measured in microns), sphere power, cylinder power, etc. The input characterization data store 214 may receive updates to the input allowed via the network communication module 240. For example, new nomograms provided by nomogram data source 116 may require an additional piece of input data.

Further, the general topographical images may be revised to add an additional image for observed corneal topography that does not closely match any of the existing images, and/or additional sub-patterns may be specified. The input characterization data store 214 may also receive updates to acceptable ranges of input parameters. For example, the acceptable range of input parameters for a particular piece of data may be revised over time as best practices and measurement methods change.

A parameter calculation module 216 may calculate surgical parameters for a given patient using data from the patient data store 204. The parameter calculation module 216 may be actuated by the user interface module 212 in response to a user request. A surgical plan determination module 220 retrieves one or more nomograms from a nomogram data store 224 based on patient data and parameters calculated by the parameter calculation module 216. In various implementations, the nomogram data store 224 may be or include an extensible markup language (XML) file and an XML parser.

A presentation module 228 displays one or more of the nomograms to a user via the user interface module 212. When multiple nomograms are selected, one nomogram may be presented as a default or recommended treatment plan. Others of the nomograms may be displayed in response to requests from the user interface module 212.

A surgical plan selection module 232 selects one of the displayed nomograms according to user input from the user interface module 212. In situations where only a single nomogram is present, the surgical plan selection module 232 may automatically select that surgical plan. Alternatively, the surgical plan selection module 232 may wait for the single surgical plan to be approved by a user through the user interface module 212.

The user may specify a desire to order implants according to the selected surgical plan. For example, an ICRS ordering module 236 may prepare an order for the ICRS or ICRSs as specified by the selected surgical plan. Such an order may be displayed, saved, or printed for submission by a user, such as clerical staff in a surgery practice. In some instances, the ICRS ordering module 236 may electronically submit an order to a supplier, distributor, or manufacturer of ICRSs via the network communication module 240. In some surgical plans, different manufacturers are specified, and therefore the ICRS ordering module 236 may be configured to contact each of the manufacturers and/or their suppliers to obtain the specified ICRSs. In other implementations, the ICRS ordering module 236 may identify a single distributor that can provide all of the specified ICRSs and submit the order to that supplier.

The network communication module 240 may also be used by the nomogram data store 224 to receive and/or update nomograms, such as from the nomogram data source 116 shown in FIG. 1A. In various implementations, the nomogram data store 224 may request only updated or all nomograms from the nomogram data source 116. For example, an XML file may be requested using the simple object access protocol (SOAP). In various implementations, the nomogram data store 224 may store only a single nomogram at a time, and retrieve each nomogram as necessary over the network communication module 240. In such an implementation (not shown), the nomogram data store 224 may receive patient data and calculated parameters from the parameter calculation module 216, which would be provided over the network communication module 240 to a source of nomograms, such as the nomogram data source 116.

Figures 2A, 2B:
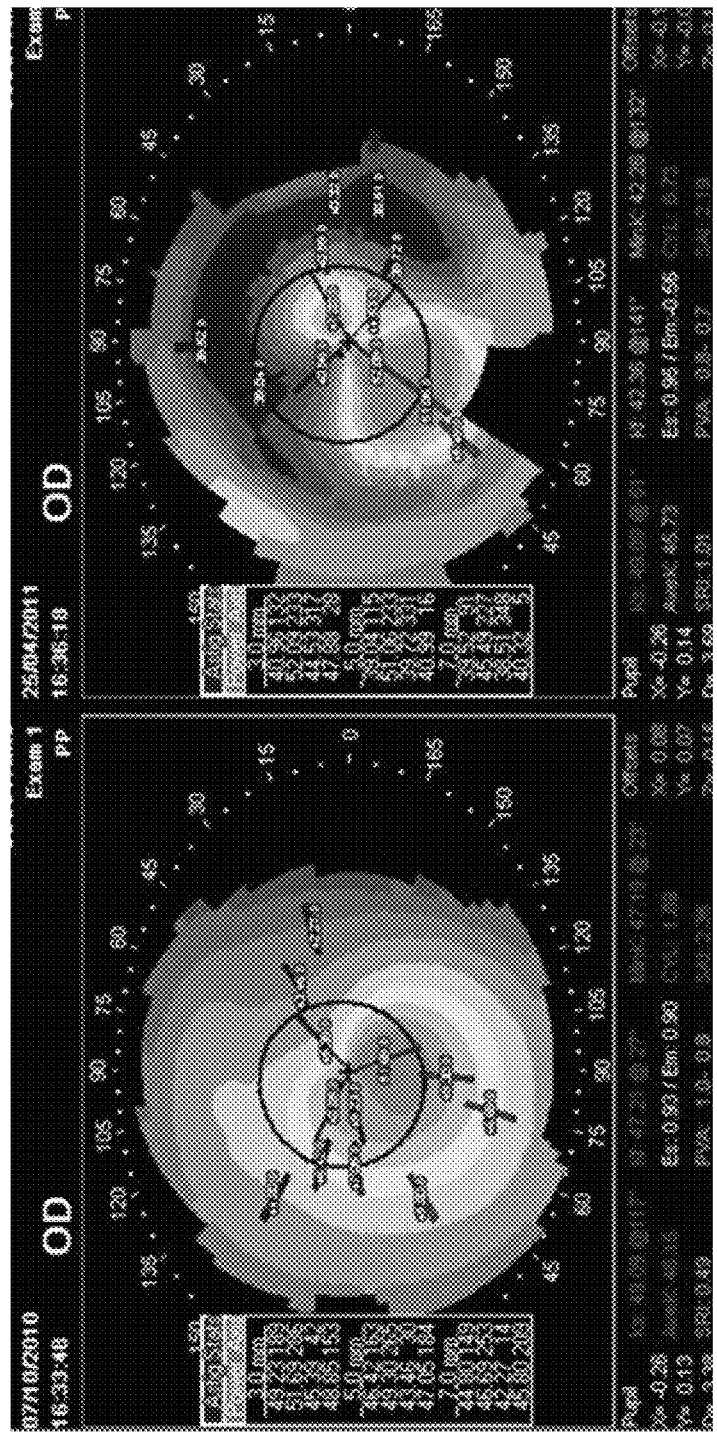
FIGS. 2A-2B are graphical representations of example corneal topographical imaging.

FIGS. 2A-2B illustrate example corneal topography information. The shading indicates the deviation of the cornea from perfect sphericity. For example, in FIG. 2B, the shading depicts a pattern described below as a "snowman," the identification of which will guide the selection of treatment options.

Figure 3:
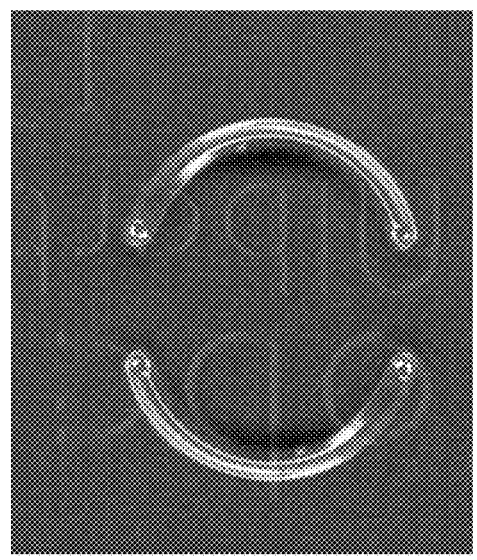
FIG. 3 is a picture of a pair of example ICRSs.

FIG. 3 shows a pair of ICRSs for illustration. For example only, available ICRS types may include INTACS implants from Addition Technology Inc., and FERRARA RING implants and KERARING implants from Mediphacos Ltda of Brazil.

Figure 4:
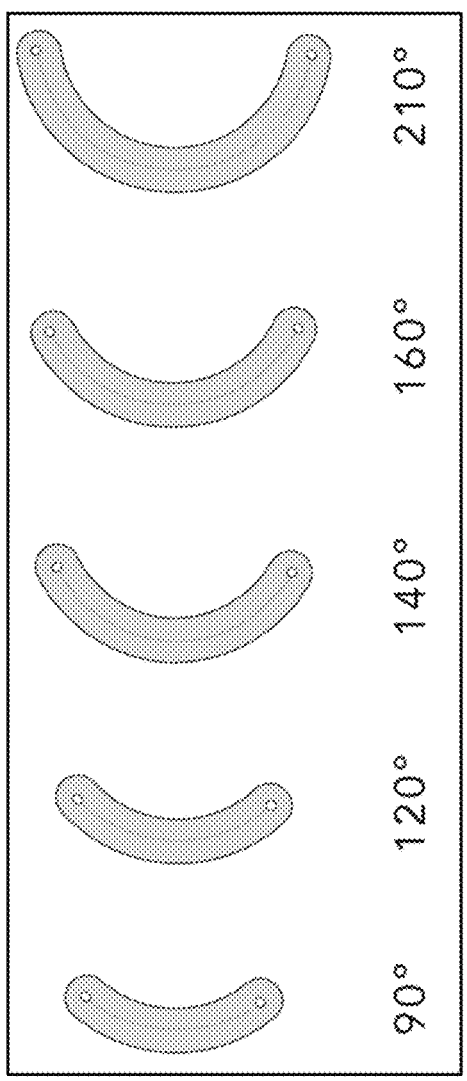
FIG. 4 is a graphical representation of ICRSs having different arcs lengths.

FIG. 4 depicts examples of variation of one of the characteristics that identifies a particular ICRS—specifically, angle, or arc length. Graphical representations of five ICRSs, ranging from 90° to 210°, are shown.

Figure 5:
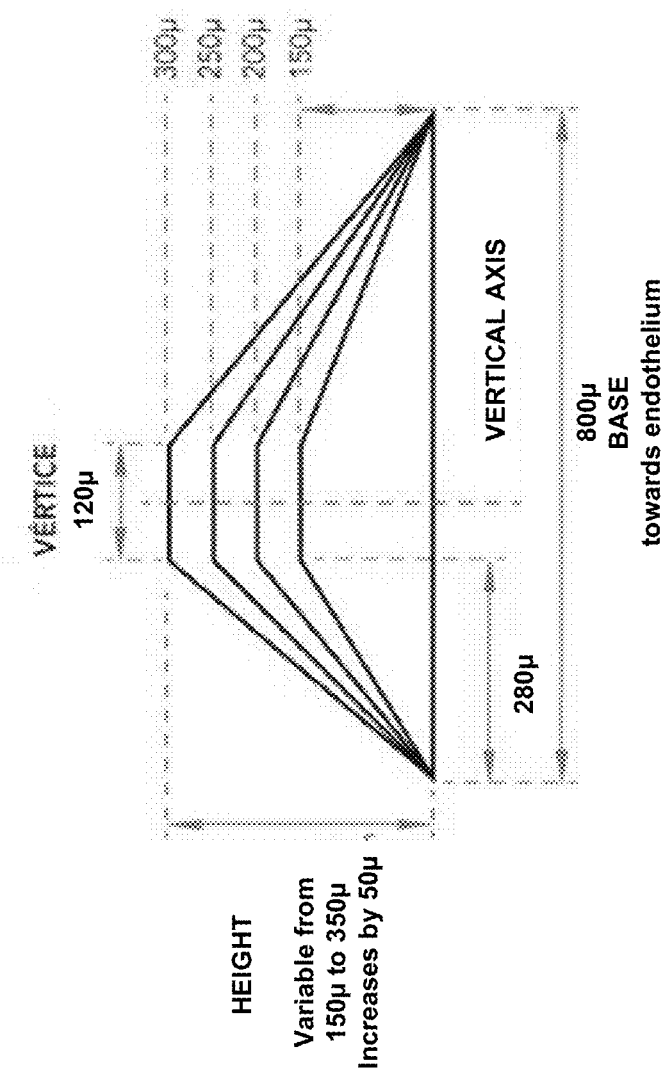
FIG. 5 is a stacked cross-sectional view of ICRSs having different parameters.

FIG. 5 depicts another characteristic that identifies particular ICRSs—thickness. Cross-sectional view of multiple ICRSs having different thickness values from 150 microns to 300 microns are overlaid on top of each other. In general, thicker ICRSs provide greater correction to corneal topography.

Figure 6D:
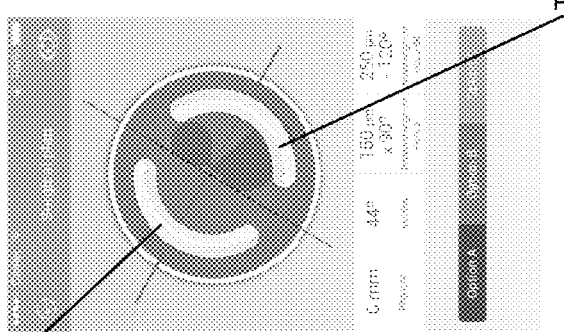
FIGS. 6A-6D are screenshots of an example graphical user interface showing surgical plans for varying corneal topography patterns.
Figure 6C:
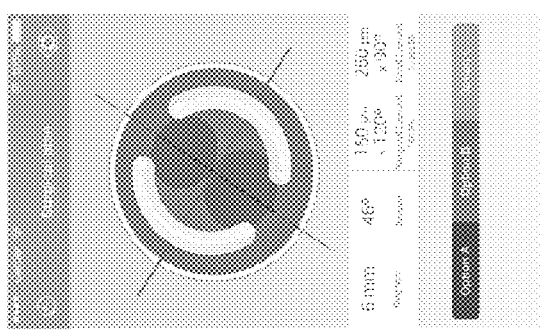
Figure 6B:
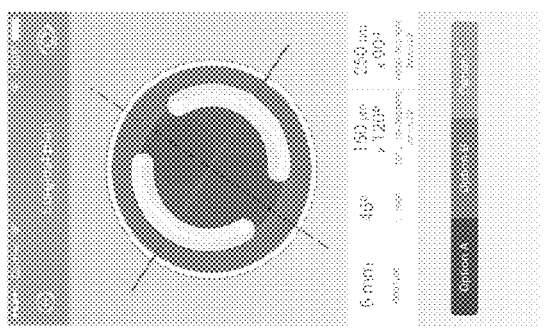
Figure 6A:
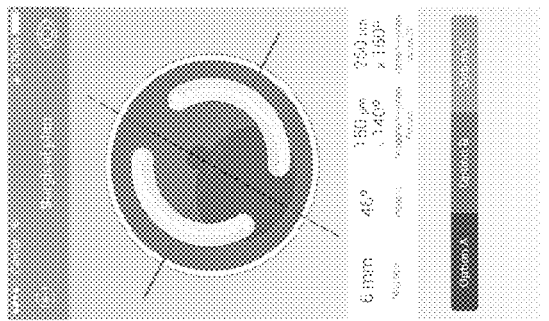

FIG. 6A is a screenshot showing three surgical plan options, option A, option B, and option C, each specified by a nomogram. For example only, the options may be sorted in order of expected effectiveness, with option A expected to produce the best results, and option C expected to produce either less beneficial results than either options A or B or less likely to produce the beneficial results of options A or B. While three options are shown, more or fewer options may be presented. In some implementations, the number of options may depend on the patient data input. For example, given certain patient data, there may only be a single nomogram that is relevant to treatment.

Options B and C may be selected if the surgeon believes there is some reason that Option A would be less effective for this patient than generally expected. For example, complex topography data that does not exactly correspond to the generic shape pictured may lead to the surgeon selecting a different option for surgery.

FIGS. 6B-6D show additional topographical shapes and corresponding suggested surgical parameters. The example surgical parameters of FIGS. 6A-6D may rely on more patient data (not shown) than simply the general shape, as described in more detail below.

FIGS. 6A-6D each show surgical parameters for ICRS implantation, including the type of ICRS, the angle at which an incision should be made, and specifications of each ICRS. Some corneal topography can best be corrected with a single ICRS (example below). In addition, certain corneal topography may be corrected nearly as accurately with a single ICRS as compared to two ICRSs, with a corresponding reduction in ICRS costs, surgery time, and in some circumstances, recovery time.

By convention, one of the ICRS is labeled as the temporal segment as the nasal segment. In FIG. 6A, the segments are labeled assuming that the depicted surgical data corresponds to a patient's left eye. The temporal segment is so named because it is located closer to the patient's temple. Meanwhile, the nasal segment is so named because it is closer to the patient's nose.

Each of the images in FIGS. 6A-6D show a perpendicular set of axes, where the axis that does not intersect either of the ICRSs is the incision axis, and the other axis, which bisects the ICRSs, may be referred to as the flat axis. If the incision angle is horizontal in the image, neither segment would be closer to the patient's nose or temple and therefore a convention has arisen where the top (superior) ICRS is referred to as the nasal segment, while the bottom (inferior) ICRS is referred to as the temporal segment. Each ICRS may be specified by manufacturer, ring type, product line, thickness, and angle. In various implementations, such as those shown in FIGS. 6A-6D, the ring type may be the same for both ICRSs.

FIGS. 7-9, 10A-10D, and 11A-11D are screenshots showing steps of determining a surgical plan for treating keratoconus in a patient's cornea when using an example user interface according to the principles of the present disclosure.

Figure 7:
FIGS. 7-9 are screenshots of an example graphical user interface for a computer-assisted ophthalmological surgical system.

FIG. 7 shows a graphical user interface for an application that can assist an ophthalmologist in diagnosing and treating keratoconus. The present disclosure generally relates to keratoconus treatment plan selection from nomograms. The nomograms described herein are referred to as "specified nomograms" (in FIG. 7, they are accessed by a link labeled "Normogram by Albertazzi" in reference to the last name of the inventor), and may generally be based on cone eccentricity. When a user of the graphical user interface desires to use alternative nomograms (such as nomograms provided by a company, such as an ICRS manufacturer), an alternative source of nomograms may be consulted. For example, a nomogram source maintained by a company may be consulted or a specific request may be sent to a third party provider to receive alternative nomograms.

Figure 8:

FIG. 8 is a graphical user interface for ectasia type selection by a user. The present disclosure primarily relates to specified nomograms for keratoconus treatment plan selection for a primary ectasia type. When another ectasia type is selected, a personalized treatment plan may be developed.

Figure 9:
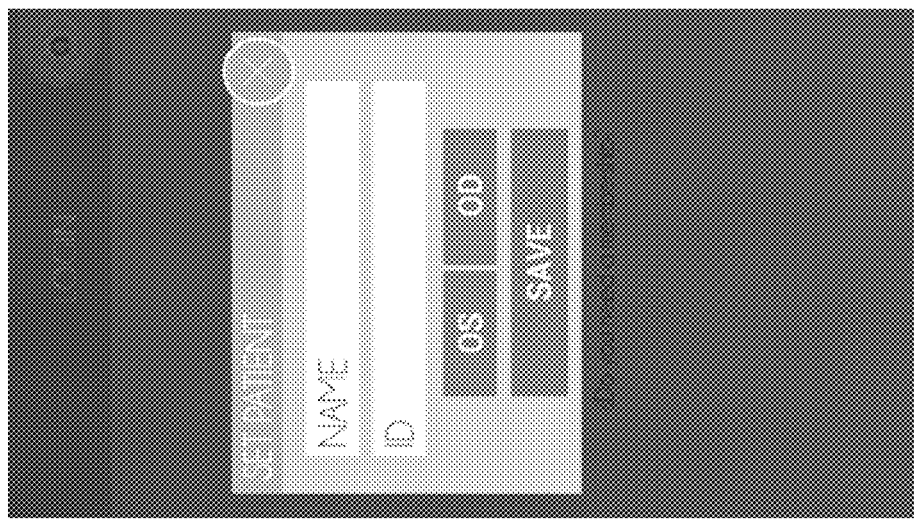

FIG. 9 is a graphical user interface for patient data input by an operator. For example, a name and/or ID (unique identifier) of the patient can be entered. In addition, the eye of the patient is selected, where OS (oculus sinister) refers to the left eye and OD (oculus dextrus) refers to the right eye.

Figures 10A, 10B, 10C, 10D:
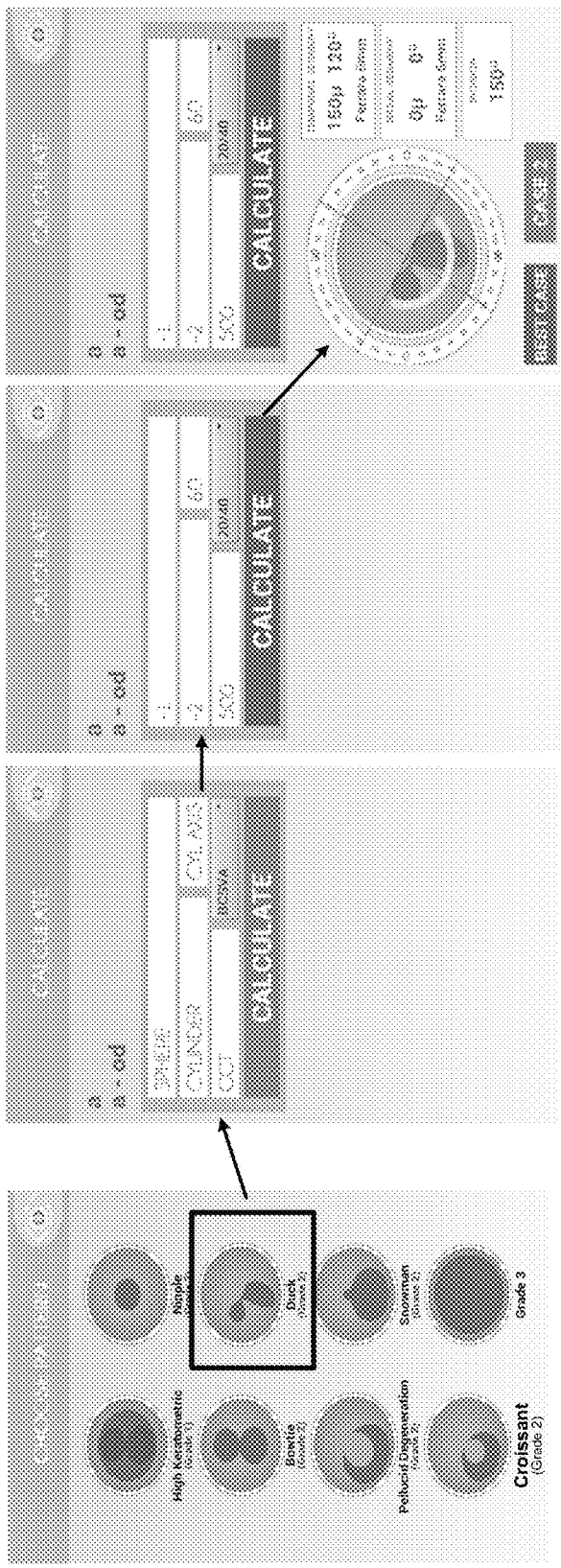
FIG. 10A-10D are screenshots of an example graphical user interface being used to specify parameters of an eye and to display corresponding surgical operation parameters.

FIGS. 10A-10D depict example screenshots of an example user interface for an operator to enter eye-related data into a computer system. When planning a surgical plan for a patient, the operator measures an anterior surface of the cornea to acquire eye topography of the selected patient. The operator identifies a shape from a predefined set of shapes that best matches the measured topographic data. These shapes may be presented graphically as shown in FIG. 10A.

In FIG. 10B, the computer system presents an input form to allow the operator to provide numerical parameters once the topographic pattern is chosen. This input form may be a pop-up window, a child window, etc. The form may include, for example only, a sphere power textbox, a cylinder power textbox, a pachymetry textbox, a cylinder axis (i.e., a refractive axis) textbox, and a BCSVA (which may be measured on a Snellen Visual Scale from 20/20-20/2000) dropdown list.

FIG. 10C depicts example data having been entered to the graphical user interface. The example data is a sphere power of −1, a cylinder power of −2, a pachymetry of 500, a cylinder axis of 60, and a BSCVA of 20/40. A calculate user interface element may then be actuated to cause surgical parameters to be calculated and one or more treatment plans to be identified from a corresponding nomogram.

FIG. 10D shows an example nomogram for treatment of keratoconus based on the data provided in FIGS. 10A and 10C. As seen, similar data to that of any one of FIGS. 6A-6D is shown, including an incision angle and identification of an ICRS. Note that, unlike previous examples, the relevant nomogram includes a single ICRS. Note also that "BEST CASE" and "CASE 2" user interface elements are present. By default, the nomogram corresponding to the "BEST CASE" may be displayed by default. Actuating the "CASE 2" user interface element will display a different nomogram that may include a different incision angle, a different ICRS, or even a second ICRS. Display may revert to the "BEST CASE" when the operator actuates the "BEST CASE" user interface element.

FIG. 11A repeats the primary topographic patterns shown in FIG. 10A for further explanation. The topographic patterns may include, for example only, shapes labeled as bowtie, croissant, duck, pellucid marginal degeneration, high keratometric, nipple, snowman, and grade 3. For some patterns, there may be sub-patterns to account for variation from the main pattern shape. The sub-patterns may vary in asymmetric grade, size, and/or shape. For example only, the bowtie pattern may have sub-patterns of small bowtie, large bowtie, asymmetric bowtie, and asymmetric bowtie inverted. For example only, the snowman pattern may have the sub-patterns of (standard) snowman and snowman without central component. For example only, the nipple pattern may have sub-patterns of large nipple and small nipple.

Figure 12B:
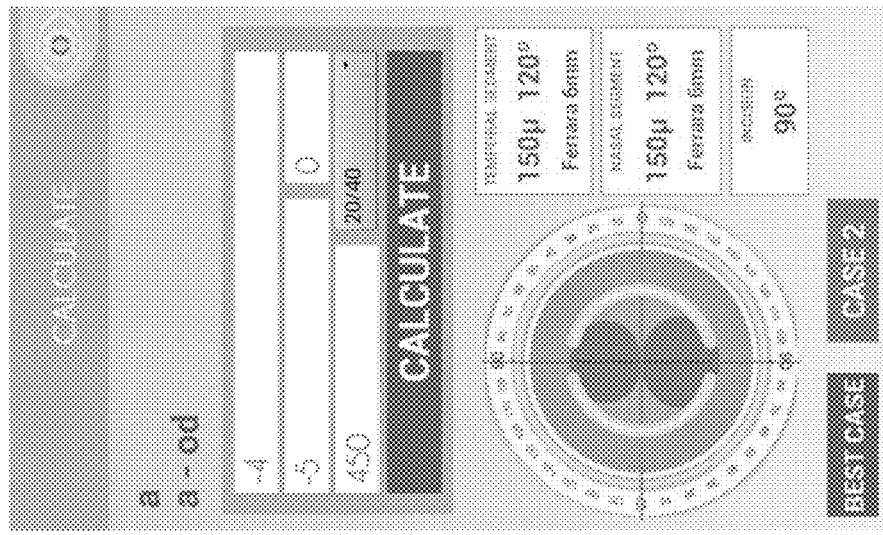
FIGS. 12A-12B are screenshots of an example graphical user interface.
Figure 12A:
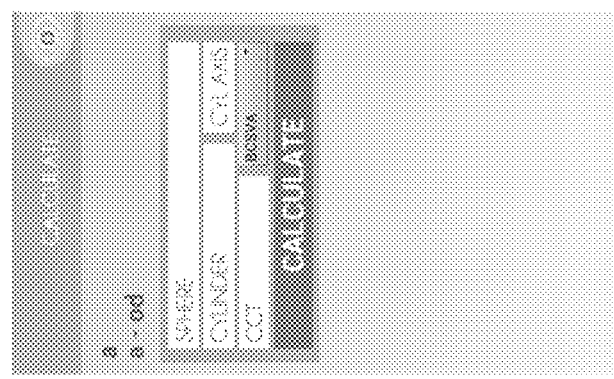

FIGS. 12A-12B are screenshots depicting another incision axis angle calculation. When the entered cylinder axis is 0°, the incision axis angle may be set to be 0°+90°=90° as described in more detail below.

Figure 13A:
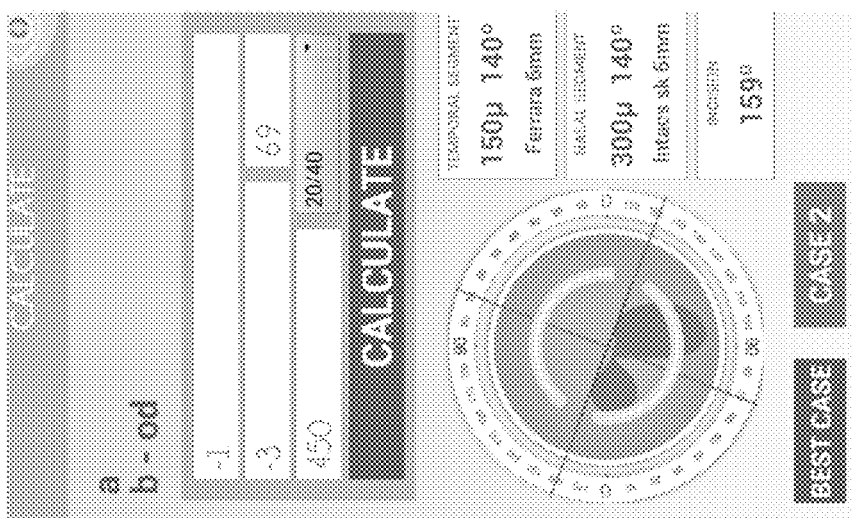
FIGS. 13A-13C are screenshots of an example graphical user interface depicting incision axis angles for different cylinder axis values.
Figure 13B:
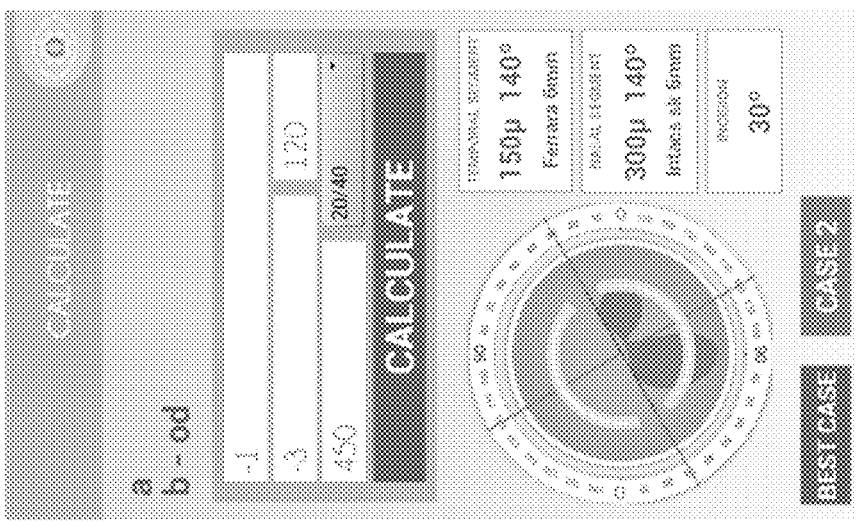
Figure 13C:
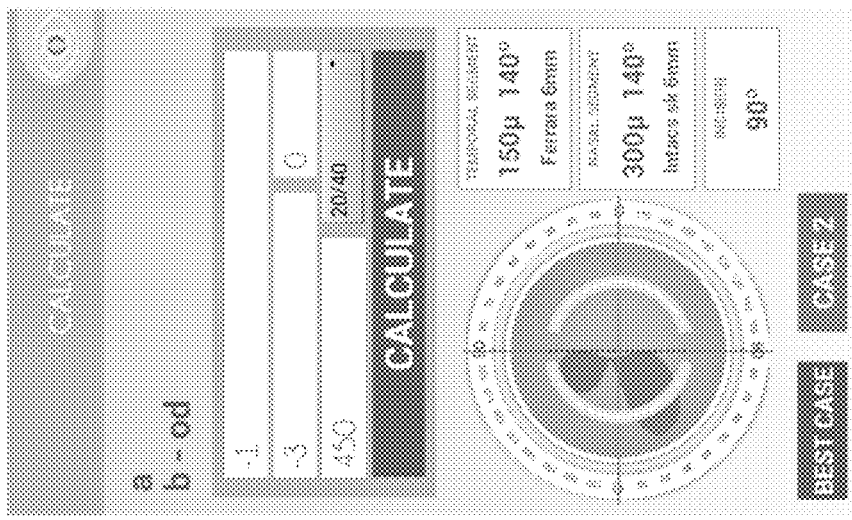

FIGS. 13A-13C are screenshots of further examples showing different calculated incision axis angles based on different entered cylinder axes for a common topographic pattern.

Figure 14:
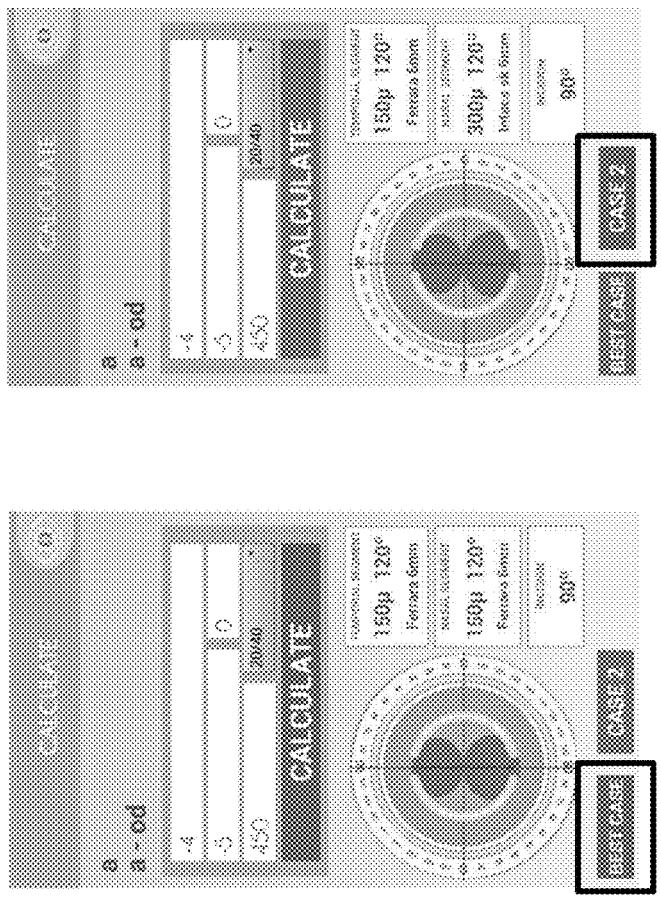
FIG. 14 is a graphical representation of how user interface elements map to treatment options in a data structure according to the principles of the present disclosure.

FIG. 14 is an illustration of the mapping relationship between the identified multiple treatment options and the calculated operation parameters. The example shown in FIG. 14 includes two identified options, "BEST CASE" and "CASE 2". The two cases map to entries in a data structure or data store, such as an XML file or a relational database. For example only, an excerpt of a data structure is reproduced here:

...
<item ESF="−5/−4" CYL="−5">
  <plan Option="1" ring="fr6" MT="150" DT="120" MN="150" DN="120"/>
  <plan Option="2" ring="frsk6" MT="150" DT="120" MN="300" DN="120"/>
</item>
<item ESF="−4" CYL="−6">
  <plan Option="1" ring="fr6" MT="150" DT="140" MN="150" DN="140"/>
  <plan Option="2" ring="fr6" MT="150" DT="120" MN="150" DN="90"/>
</item>
...

An item in the data structure is identified by matching a calculated sphere power (e.g., −4 in FIG. 14) with an ESF (which stands for sphericity) parameter range and a calculated cylinder power (e.g., −5 in FIG. 14) with a CYL (which stands for cylindrical power) parameter range of the data structure. Once mapped, options of the matched item are the identified options. In this case, option 1 may be labeled as the "BEST CASE" in FIG. 14 and option 2 is "CASE 2" in FIG. 14. Each option describes a set of ICRS specifications. Note that, in this implementation, the ESF range ("−5/−4") for the identified item in the data structure corresponds to a range between −5 and −4 inclusive.

Figure 15:
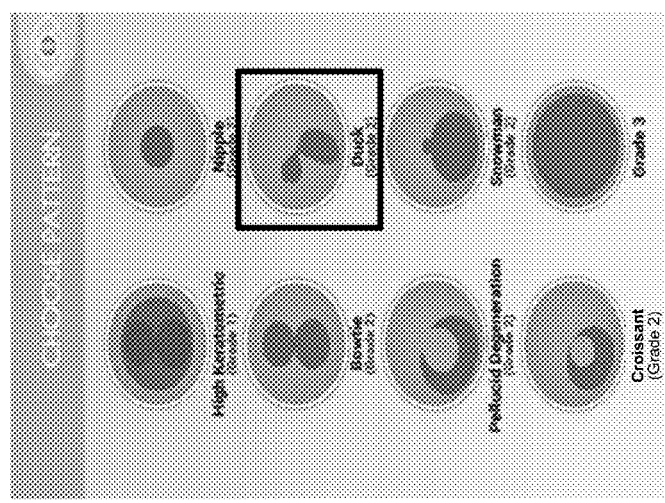
FIG. 15 is a graphical representation of how a topographical shape maps to a data structure according to the principles of the present disclosure.

FIG. 15 shows an illustration of how a set of nomograms may be grouped together under a single topographic pattern heading, and thereby selected in response to the operator identifying a topographic pattern in a user interface. For example only, an excerpt of a data structure corresponding to the selected "Duck" pattern is reproduced here:

```
. . .
<nomogram name="duck">
<item ESF="0/1" CYL="-2/2">
    <plan Option="1" ring="sk6" MT="300" DT="150" MN="0" DN="0"/>
    <plan Option="2" ring="fr6" MT="150" DT="120" MN="0" DN="0"/>
</item>
<item ESF="-1/1" CYL="-3">
    <plan Option="1" ring="frsk6" MT="150" DT="140" MN="300" DN="130"/>
    <plan Option="2" ring="fr6" MT="150" DT="140" MN="0" DN="0"/>
</item>
<item ESF="-1/1" CYL="-4">
    <plan Option="1" ring="frsk6" MT="150" DT="140" MN="300" DN="130"/>
    <plan Option="2" ring="fr6" MT="150" DT="140" MN="0" DN="0"/>
</item>
<item ESF="-1/1" CYL="-5">
    <plan Option="1" ring="frsk6" MT="200" DT="140" MN="350" DN="130"/>
    <plan Option="2" ring="fr6" MT="150" DT="140" MN="150" DN="90"/>
</item>
<item ESF="-1/1" CYL="-6">
    <plan Option="1" ring="frsk6" MT="200" DT="140" MN="350" DN="130"/>
    <plan Option="2" ring="fr6" MT="150" DT="140" MN="150" DN="120"/>
</item>
. . .
```

Figure 16:
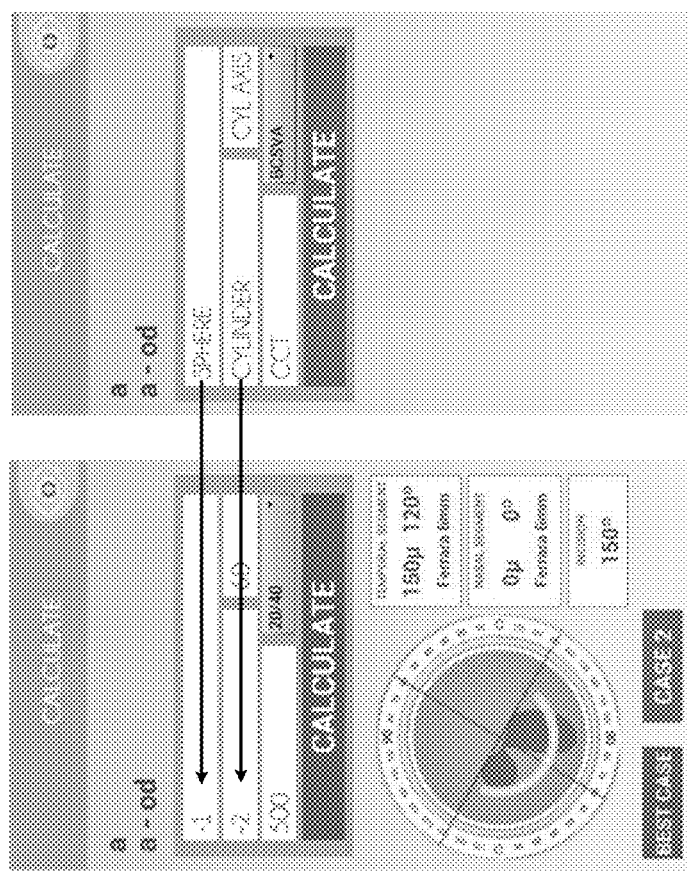
FIG. 16 is a graphical representation of how input data maps to a data structure according to the principles of the present disclosure.

FIG. 16 shows an illustration of multiple treatment options related to one pair of calculated sphere power and cylinder power in an xml file. For example only, an excerpt of a data structure is reproduced here, where the sphere value of −1 and the cylinder value of −2 select the first item in the following excerpt:

```
. . .
<item ESF="-1" CYL="-2">
    <plan Option="1" ring="fr6" MT="150" DT="120" MN="0" DN="0"/>
    <plan Option="2" ring="frsk6" MT="150" DT="120" MN="300" DN="150"/>
</item>
<item ESF="-3/-2" CYL="-1">
    <plan Option="1" ring="sk6" MT="300" DT="150" MN="300" DN="150"/>
    <plan Option="2" ring="frsk6" MT="150" DT="120" MN="300" DN="150"/>
</item>
. . .
```

Figure 17:
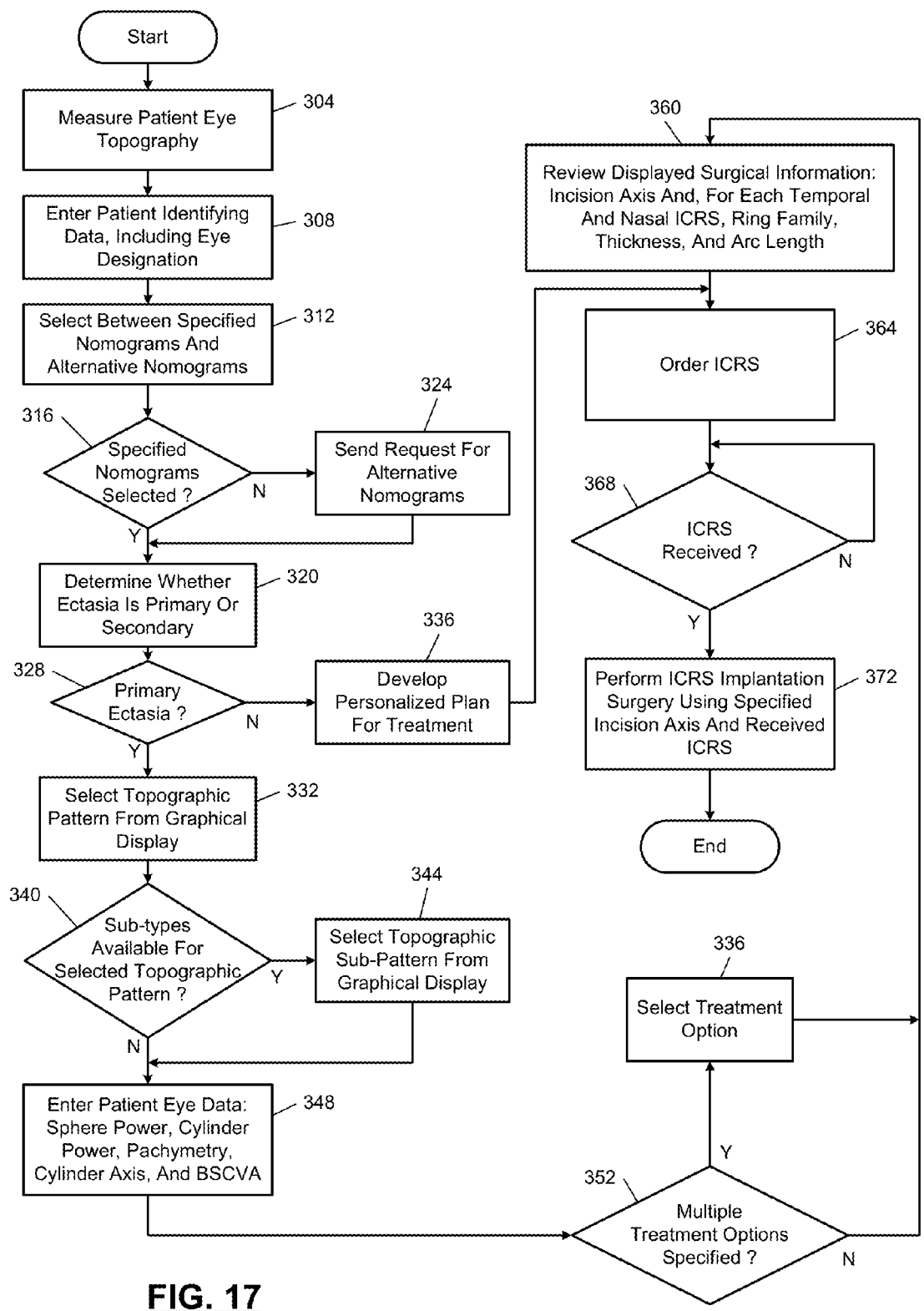
FIG. 17 is a flowchart of an example method of treating keratoconus including selecting a surgical plan.

In FIG. 17, an example method of treating keratoconus, such as by an ophthalmological surgeon, begins at 304, where patient corneal topography is measured. For example, the anterior surface of the cornea may be mapped. At 308, the surgeon enters patient identifying data, such as a patient I.D. number. Further, the subject eye (either left or right) is identified. The patient identifying data is entered into a computer assisted ophthalmological surgical system.

At 312, using the computer-assisted system, the surgeon may select between specified nomograms and alternative nomograms. The specified nomograms may be specified by a developer of the computer-assisted system or by a third party. In various implementations, the specified nomograms may be predefined when the computer-assisted system is acquired or used by the surgeon.

At 316, if specified nomograms are selected, control continues at 320; otherwise, control transfers to 324. At 324, control sends a request for alternative nomograms. For example, this request may be sent to a manufacturer of ICRSs. Once a response to the request is received, control transfers to 320.

At 320, the surgeon determines whether the ectasia is primary or secondary (such as post-Lasik or post-keratoplasty). At 328, if the surgeon determines that the ectasia is primary, control transfers to 332; otherwise, control transfers to 336. At 332, the surgeon selects a topographic pattern from a graphical display of the computer-assisted system that best matches the topography of the patient's eye from 304.

If there are sub-patterns available for the selected topographic pattern, control transfers to 344; otherwise, control transfers to 348. At 344, the surgeon selects a sub-pattern from the graphical display that best matches the eye topography of 304. Control then continues at 348. At 348, the surgeon enters patient eye data such as sphere power, cylinder power, pachymetry, cylinder axis, and best spectacle corrected visual acuity (BSCVA).

Control continues at 352 where, if multiple treatment options are specified, control transfers to 356. If only a single treatment option is specified, control transfers to 360. At 356, the surgeon selects one of the treatment options and control continues at 360. At 360, the surgeon reviews displayed surgical information on the computer-assisted system, including incision axis and for each of the temporal and nasal ICRSs, the ring family, thickness, and arc length. Control continues at 364, where a surgeon places an order for the ICRSs needed to perform the selected surgery.

Returning to 336, the surgeon develops a personalized plan for treatment of a patient and control proceeds to 364. Following 364, control remains at 368 until the ICRSs are received, at which point control transfers to 372. At 372, the surgeon performs ICRS implantation surgery using the specified incision axis and the received ICRSs. Control then ends. If both eyes of the patient are to be operated upon, control elements 304 through 360 may be repeated twice, while a single order can be placed for all of the necessary ICRSs at 364. The ICRS implantation surgery of 372 may then be performed sequentially on each eye.

Figure 18A:
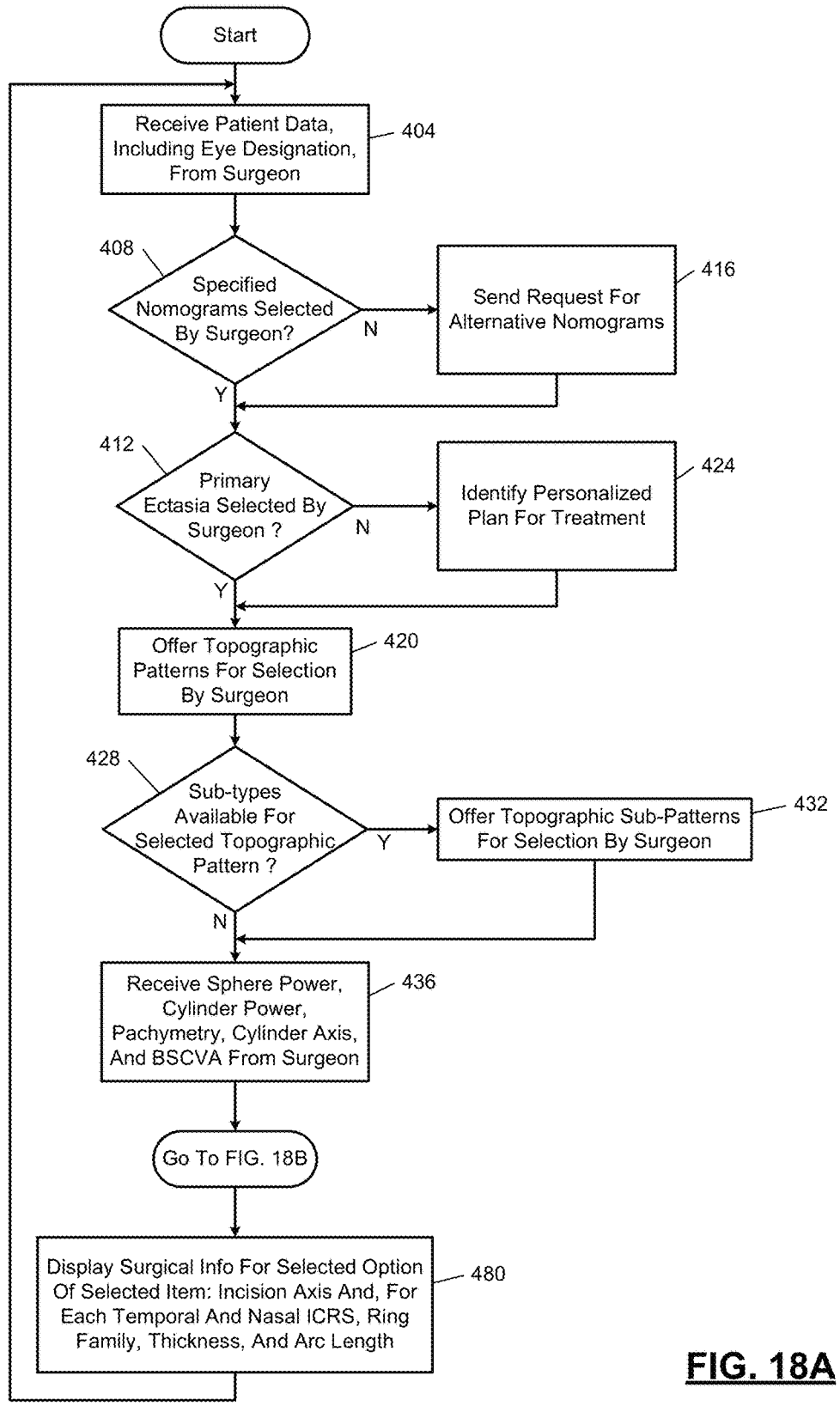
FIGS. 18A-18B together are a flowchart of a computerized method of developing a surgical plan for the treatment of keratoconus.
Figure 18B:
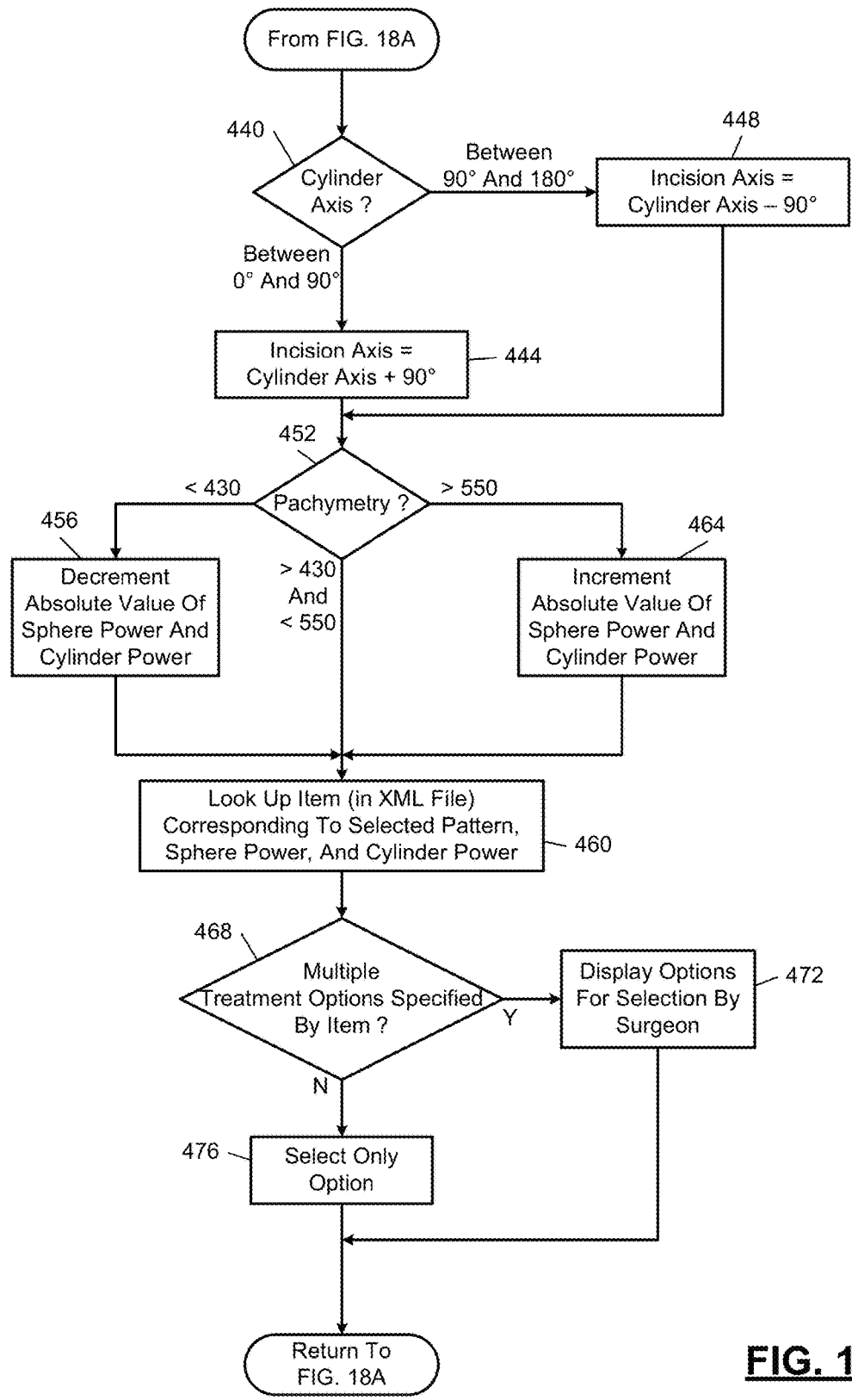

In FIGS. 18A-18B, example operation of a computer system for the treatment of keratoconus is presented. Control begins at 404, presenting data input forms at which patient data can be received, such as from a surgeon. The patient data may include a unique identifier of the patient and a designation of whether the left or right eye is to be operated upon.

Control continues at 408, where based on a selection by the surgeon, control transfers to 412 when the specified nomograms are selected and transfers to 416 when alternative nomograms are selected. At 416, control sends a request for alternative nomograms, such as to an alternative nomogram source. When a response is received, control transfers to 412.

At 412, control offers a selection of ectasia to the surgeon. If the surgeon selects primary ectasia control transfers to 420; otherwise, control transfers to 424. At 424, a personalized plan for treatment is identified by the surgeon and control then continues at 420. At 420, control offers topographic patterns for selection by the surgeon. These topographic patterns are canonical shapes that roughly correspond to various corneal topographies that have been observed in patients.

After selection of one of the topographic patterns by the surgeon control continues at 428 where, if subtypes are available for the selected topographic pattern, control transfers to 432; otherwise, control continues at 436. At 432, control offers topographic sub-patterns for selection by the surgeon. After one of the sub-patterns is selected control continues at 436. At 436, control receives additional patient data, such as sphere power, cylinder power, pachymetry, cylinder axis, and BSCVA from the surgeon.

Control then continues in FIG. 18B at 440. At 440, if the specified cylinder axis is between 0° and 90°, control transfers to 444; if the cylinder axis is instead between 90° and 180°, control transfers to 448. If the cylinder axis is exactly 90°, in some implementations, control will transfer to 444; in other implementations, control will transfer to 448. In yet further implementations (not pictured), if the cylinder axis is exactly 90°, the incision axis will be set to 90°. At 444, control sets the incision axis to be the sum of the cylinder axis and 90°. Control then continues at 452. At 448, control sets the incision axis to be the cylinder axis minus 90° and control continues at 452.

At 452, control analyzes the specified pachymetry. If the pachymetry is less than 430, control transfers to 456; if the pachymetry is between 430 and 550, control transfers to 460; if the pachymetry is greater than 550, control transfers to 464. At 456, control decrements the absolute value of the sphere power as well as the absolute value of the cylinder power. In other words, the sign remains the same but the absolute value decreases by one. Control then continues at 460. At 464, control increments the absolute value of the sphere power and the absolute value of the cylinder power. In other words, the sign remains the same but the absolute value increases by one.

Control then continues at 460. At 460, control looks up an item (such as from an XML file) that corresponds to the selected pattern/sub-pattern, the sphere power (as adjusted), and the cylinder power (as adjusted). Control then continues at 468 where, if multiple treatment options are specified by the looked up item, control transfers to 472; otherwise, control transfers to 476.

At 472, control displays the treatment options for selection by the surgeon. Upon receiving the selection, control returns to FIG. 18A at 480. At 476, control selects the only available treatment option and returns to FIG. 18A at 480. At 480, control displays surgical information for the selected option of the looked up item. This surgical information may include a specified incision axis and specifications of one or both of a temporal ICRS and a nasal ICRS. An ICRS may be specified by ring family, thickness, and arc length.

Following surgery, the system may record surgical outcomes at various times post-surgery. These outcomes may be presented to the operator to assist in selection. These outcomes may also be used to adapt the nomograms. The adaptation may be performed manually, such as by a developer of the system, or automatically, such as using a genetic algorithm to optimize a specific set of quantifiable outcome data. The adaptation may be performed at a central location based on anonymized patient data. Operators of the system may subscribe to receive the updated nomograms.

Figure 19A:
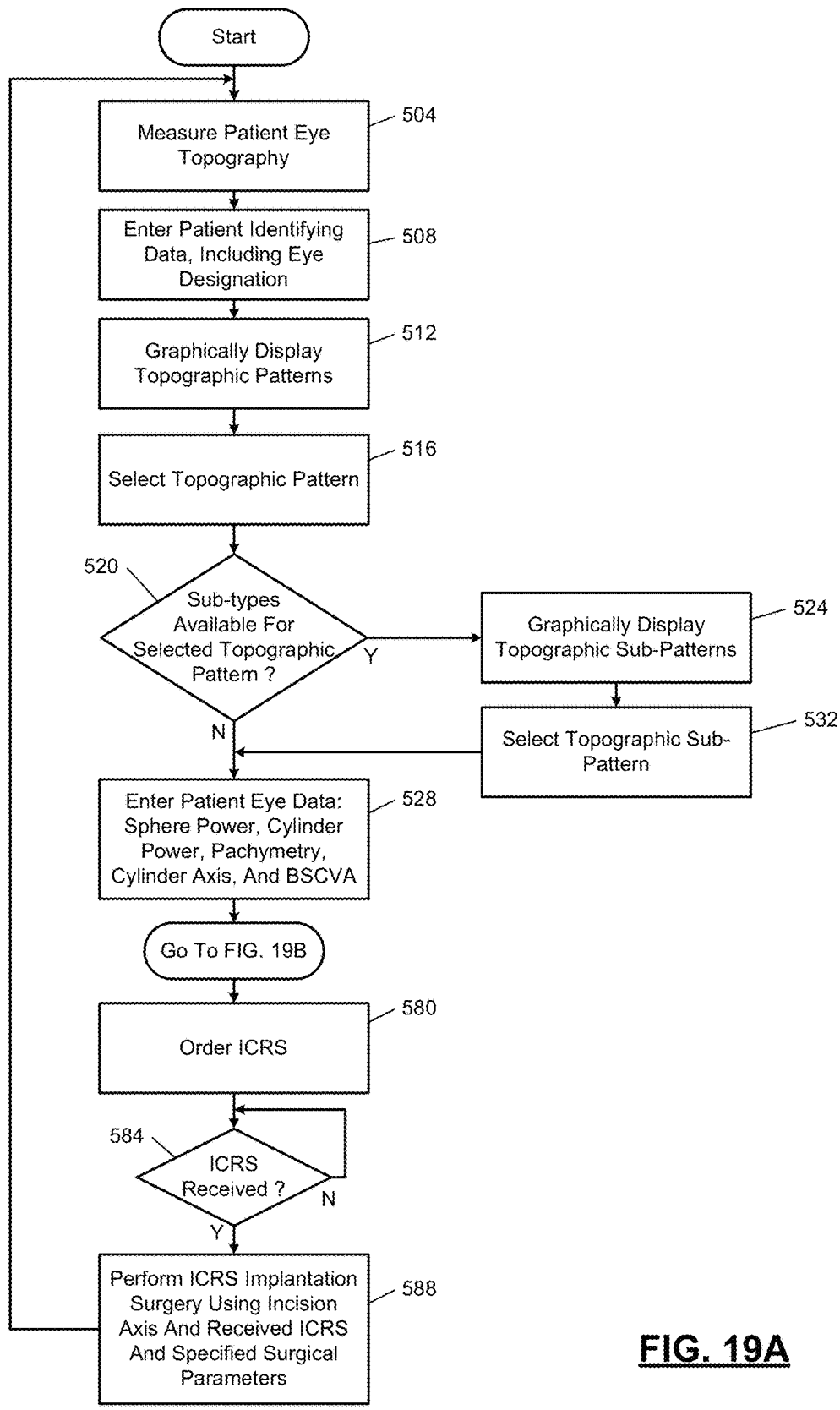
FIGS. 19A-19B together are a flowchart of a computer-assisted method of treating keratoconus.

In FIG. 19A, an example method for treating keratoconus is performed by a surgeon with the assistance of a computer system. Control begins at 504, where the patient's corneal topography is measured. This measurement may be performed by the surgeon or by a prescribing ophthalmologist. In 508, an operator of the computer system (such as the surgeon or prescribing ophthalmologist) enters identifying data of the patient, including which eye is of interest.

At 512, the computer system graphically displays topographic patterns. At 516, the operator selects a topographic pattern that best matches the measured topography of 504. At 520, if the selected topographic pattern has subtypes available, control transfers to 524; otherwise, control transfers to 528. At 524, the computer system graphically displays the topographic sub-patterns for the selected pattern.

Figure 19B:
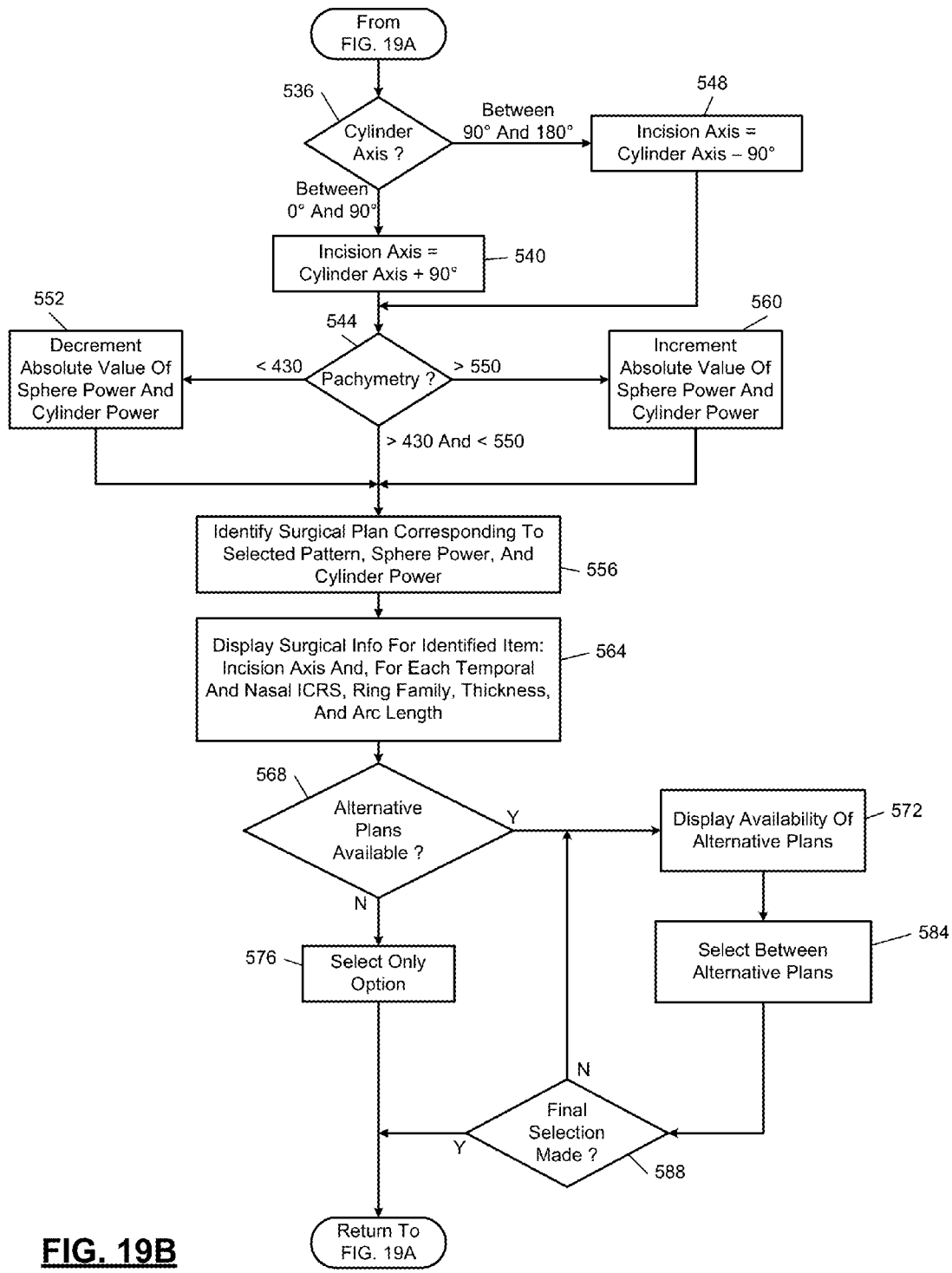

At 532, the operator selects the topographic sub-pattern that best matches the corneal topography of 504. Control then continues at 528. At 528, the operator enters patient eye data such as sphere power, cylinder power, pachymetry, cylinder axis and BSCVA. Control then transfers to 536 in FIG. 19B.

At 536, the computer system analyzes the cylinder axis. If the cylinder axis is between 0° and 90°, control transfers to 540, where the incision axis is set equal to the cylinder axis plus 90°. Control then continues at 544. Meanwhile, if the cylinder axis is between 90° and 180° at 536, control transfers to 548, where the incision axis is set equal to the cylinder axis minus 90°. Control then continues at 544.

At 544, the specified pachymetry of the user's eye is considered by the computer system. If the pachymetry is less than 430, control transfers to 552, where the absolute value of the sphere power and the cylinder power are decremented and control continues at 556. If, at 544, the pachymetry is between 430 and 550, control proceeds directly to 556. If, at 544, the pachymetry is greater than 550, control transfers to 560, where the absolute value of the sphere power and the cylinder power are incremented, and control continues at 556.

At 556, the computer system identifies a surgical plan corresponding to the selected pattern, sphere power (as adjusted), and cylinder power (as adjusted). For example, the computer system may identify an entry in a database or other data structure, where that item specifies ranges within which the sphere power falls and within which the cylinder power falls. Control continues at 554, where surgical information is displayed for the identified item. For example, this may include the incision axis and a specification of one or two ICRSs.

At 568, if the identified surgical plan includes alternative plans, control transfers to 572; otherwise, control transfers to 576. At 576, the computer system selects the only available surgical plan and returns to FIG. 19A at 580. At 572, control displays the availability of alternative plans. Control continues at 584, where the computer system allows the operator to select between alternative plans. At 588, if a final decision of a surgical plan has been made, control transfers to 580 of FIG. 19A; otherwise, control returns to 572.

At 580 of FIG. 19A, the computer system, at the direction of the operator, orders the specified ICRSs. Alternatively, the operator themselves, or a member of their staff, may order the specified ICRSs. At 584, once the ICRSs are received, control transfers to 588; otherwise, control remains at 584. At 588, the surgeon performs ICRS implantation surgery using the incision axis of the selected surgical plan and the received ICRSs.

The specified surgical parameters, which may be displayed on a screen of the computer system before and during surgery, specify which of the ICRSs should be placed at what locations in the patient's eye. In various nomograms, the two ICRSs to be implanted in a single eye will be different. In fact, according to the specified nomograms, the ICRSs may be from different manufacturers and/or different product lines from the same or different manufacturers. Nomograms promulgated by a manufacturer will, as expected, generally only recommend ICRSs produced by that manufacturer.

Referring back to FIG. 10C, the pachymetry is 500, which is between 430 and 550. Thus after calculation is done, the absolute value of the sphere power and cylinder power remain the same, as shown in FIG. 10D compared to FIG. 10C.

Meanwhile, an incision axis angle is suggested for the operation. The incision axis angle may also be referred to as an angle of the steep axis with respect to the x (horizontal) axis of the coordinate system. The incision axis angle is generally used for orienting an insertion of the ICRSs during the operation. The selected ICRS is implanted by pointing the steep axis of the ICRS at the suggested incision axis angle relative to the x-axis of the coordinate system. In the example shown in FIG. 11D, the entered cylinder axis of 60° is between 0° and 90°. Thus the suggested incision axis is set to be 60°+90°=150°. Accordingly, the specified temporal ICRS is to be implanted into the cornea of the eye with a suggested incision axis of 150°.

The identified treatment options or surgical plans of FIG. 10D also include two displaying sections, an image section and a table section. In this example, the image section shows a duck pattern and a steep axis at the incision angle (recall that the steep axis is the axis not intersecting the ICRS). In this example, the identified surgical plan option includes only one ICRS. Based on the position of the selected duck pattern, the ICRS is oriented as a temporal segment. The table section displayed in FIG. 10D includes ICRS parameters: a Ferrara ring family, length of 6 mm, arc of 120°, and thickness of 150μ.

The system may define parameters that determine whether a surgical plan can be reliably developed for a given patient. For example only, the parameters in one implementation may be:
Axial Length: 23 mm±0.5 mm
Wide-To-Wide: 12 mm±1 mm
Keratoconus with grade 1 or 2 of Amsler-Krumeich classification
Other ocular structures without alteration For patients that do not meet the previous conditions, the system may provide an option to provide data related to the patient to a developer for assessment and potential inclusion into the system. This capability may be integrated into the system. For example only, once patient data is entered into the system, if the patient is not a candidate for any of the existing surgical plans, the operator of the system (such as a surgeon or prescribing ophthalmologist) is presented with the option of uploading the patient's data to the developer for modification of the system. The patient data may be anonymized before uploading.

In other implementations, a side channel may be used. For example, the system operator may submit the patient data via a web form, via email, etc. In still other implementations, data may be sent by the system to an expert for analysis. The expert can prepare a customized surgical plan and provide the plan to the operator either through the system or through a side channel, such as via a written or emailed report.

Figure 20C:
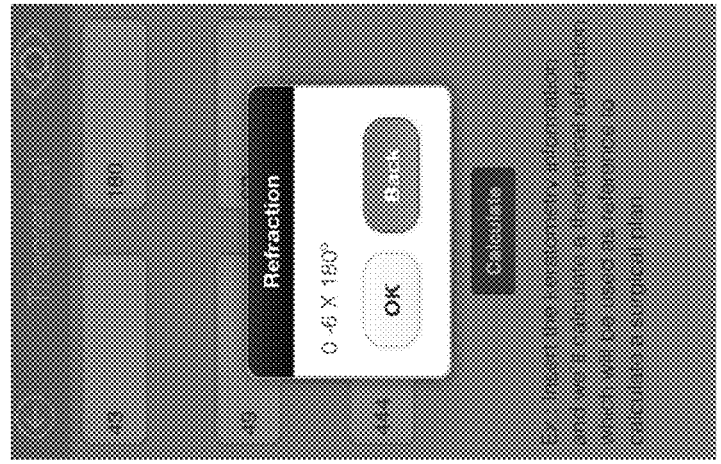
FIGS. 20A-20C are screenshots of an example graphical user interface illustrating different refraction selections.
Figure 20B:
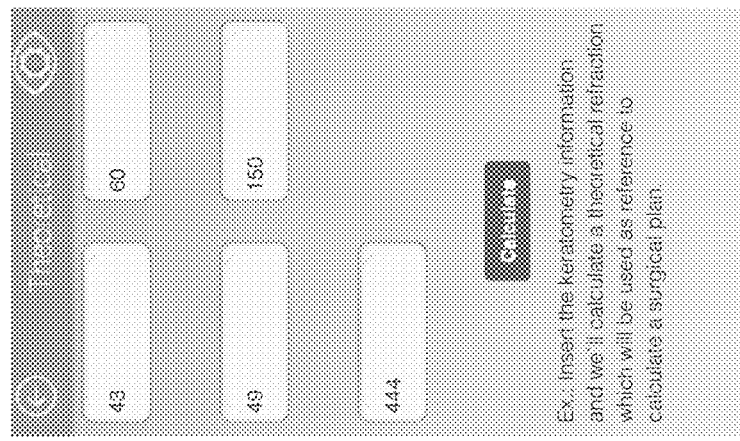
Figure 20A:
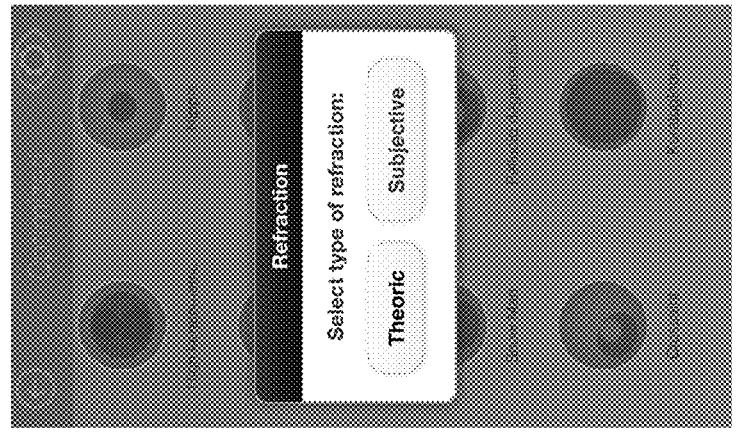

FIG. 20A depicts different refraction options provided in an example user interface. After selecting the topographic pattern, the operator may be asked to select between a subjective refraction and a keratometric refraction. The choice may be based on a subjective preference of the operator and may be guided by which data is available.

Subjective refraction (shown in FIG. 20A as a button labeled "Subjective") may generally be available at early stages of keratoconus. If reliable subjective visual acuity is not available, theoretic refraction (shown in FIG. 20A as a button labeled "Theoric") may be a better choice, which usually occurs at a more advanced state of keratoconus. As shown above, for subjective refraction, data such as the sphere power, cylinder power, cylinder axis, pachymetry, and BSCVA may be entered.

FIG. 20B shows an example user interface where parameters for a theoretic refraction calculation are inserted. These parameters may include keratometric values, axis of the steep and flat meridian, and pachymetry values. In FIG. 20C, various implementations, the system calculates a theoretic refraction for use in ICRS selection: "0–6×180°". From the entered parameters, a spherical value may be calculated as 43–K1, while a cylindrical value may be calculated as K1–K2.

Figure 21A:
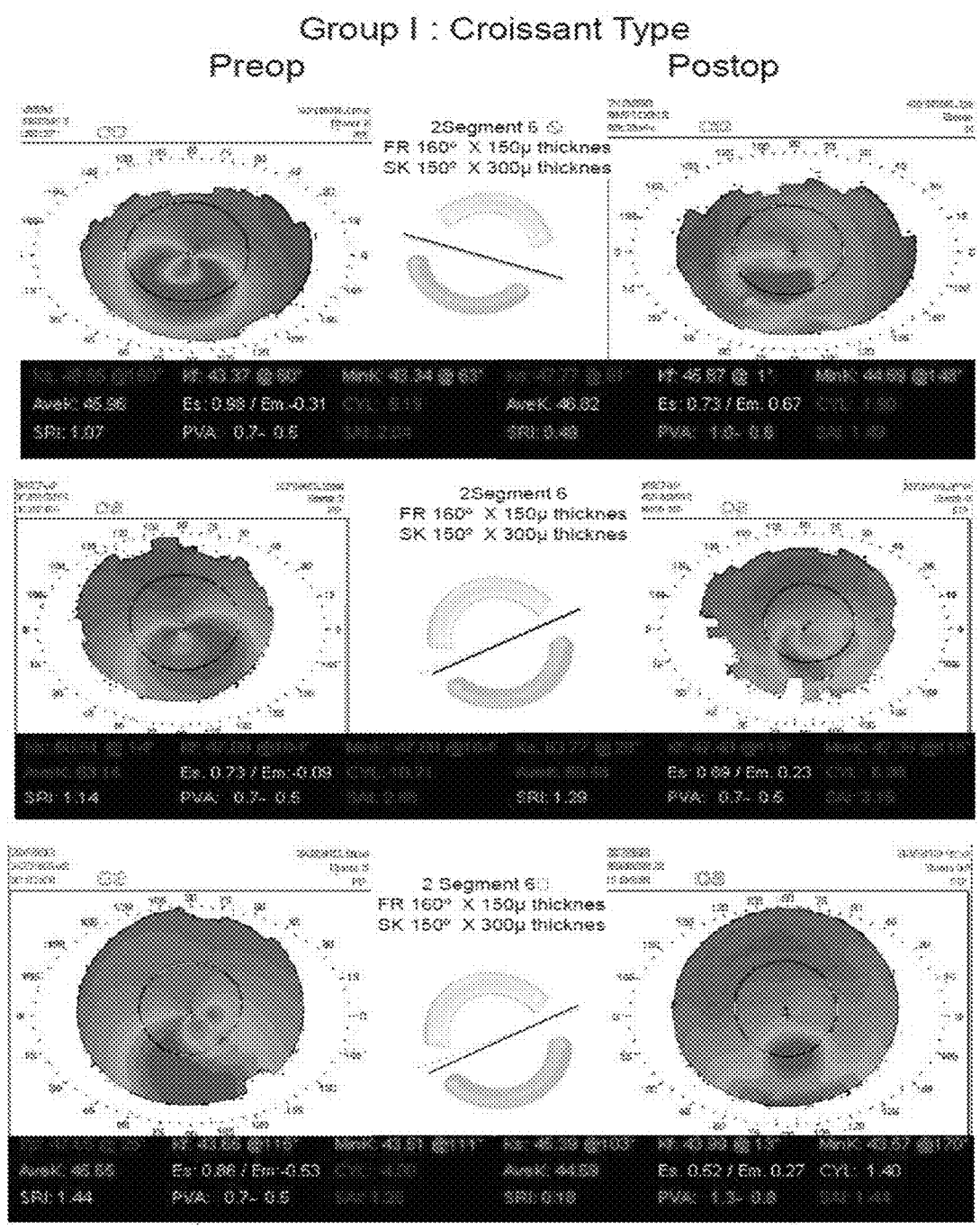
Figure 22A:
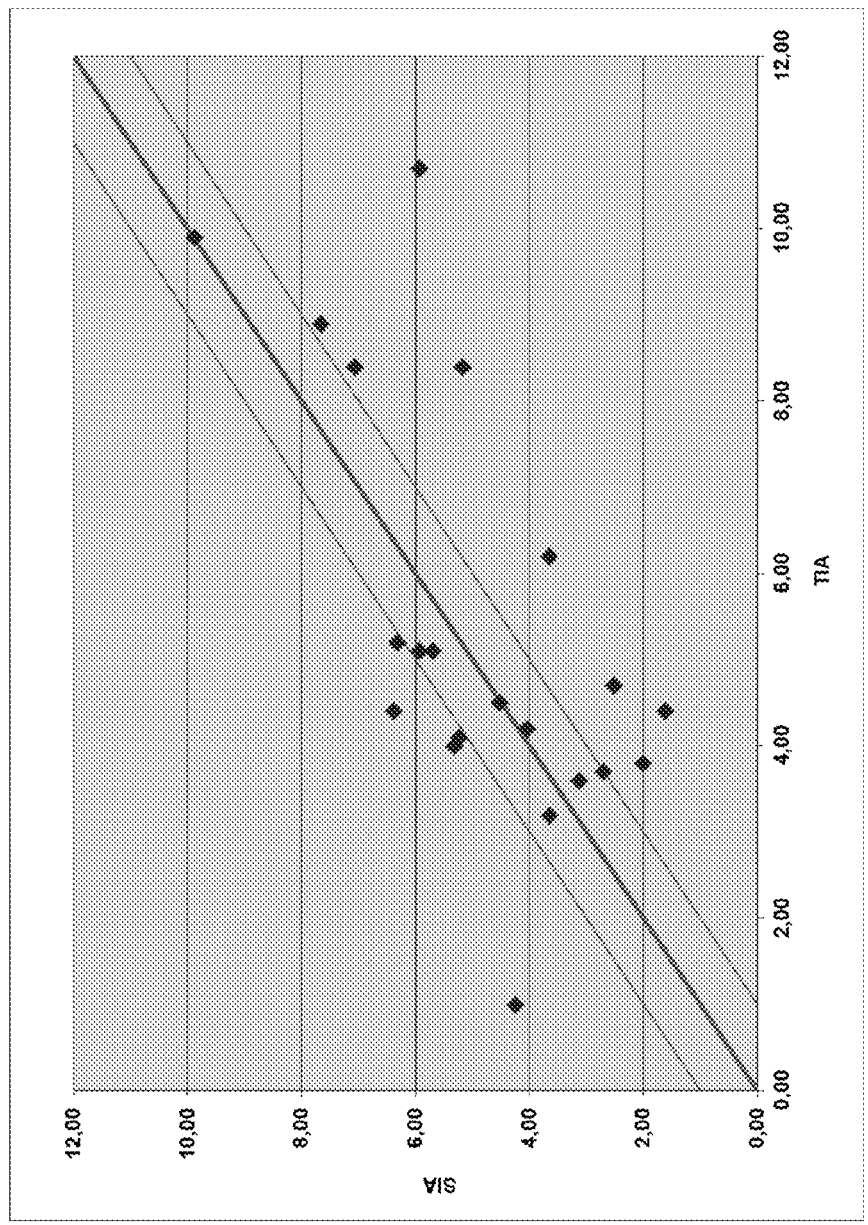
FIG. 22A is a chart of surgically induced astigmatism (SIA) vector versus target induced astigmatism (TIA) vector.
Figure 22B:
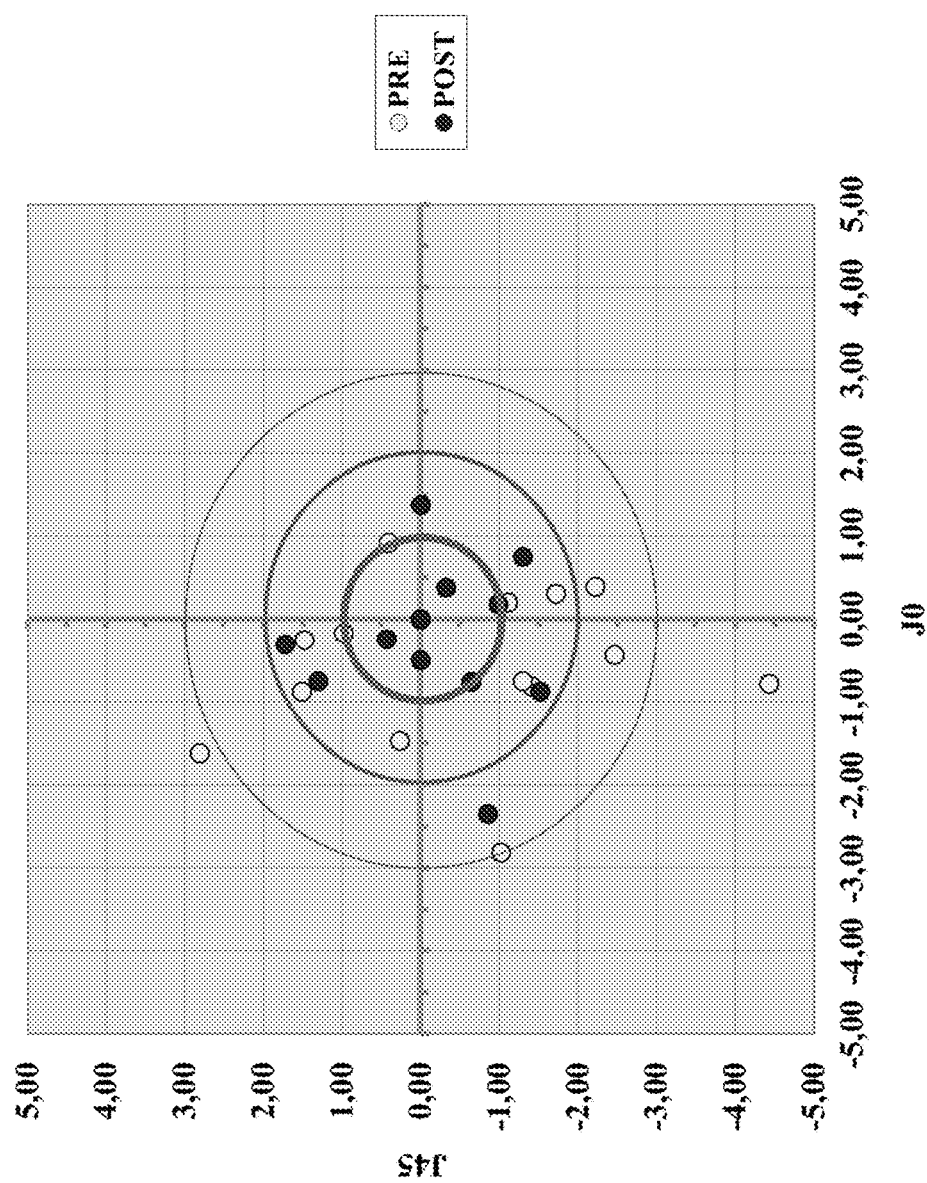
FIG. 22B is a chart of Cartesian astigmatism (J0) and oblique astigmatism (J45) both pre-surgery and post-surgery.

EXAMPLES 43 eyes of 33 patients with contact lens intolerance or progressive paracentral keratoconus underwent ICRS implantation surgery and were followed for at least 6 months. Patients were divided in two groups according to the coincidence of axis of astigmatism and coma. The groups are Group I, +/−30° coincident, having a "croissant" shape, shown in FIG. 21A, and Group II, non-coincident (30°-75°), having a "duck" shape, shown in FIG. 21B.

Surgery was performed manually and ICRS were implanted at 6 mm of the optical axis: 150° FERRARA RING implants were placed temporal-inferior and 90° INTACS implants were placed nasal-superior. No intraoperative or postoperative complications occurred in these eyes over the course of observation.

Tectonic outcomes were evaluated as a reduction of the keratometric (K) values: K minimal (Kmin) and K maximal (Kmax). Visual outcomes were measured as improvement in uncorrected distance visual acuity (UDVA), best corrected distance visual acuity (CDVA), and refractive error (myopia and astigmatism) reduction (on a decimal scale). Vectorial analysis of the astigmatism was performed using Alpins and Thibos methods. Data were processed with the R statistical programming language for descriptive and inference statistical analysis.

There was a significant (p<0.01) reduction of keratometric values in both groups, especially in Kmax:
Group 1: Pre 49.06±0.40 to post 46.37±3.43 (Kmax)
Group 2: Pre 51.25±3.95 to post 49.06±3.53 (Kmax)
UDVA gain was significant (p<0.01) in both groups:
Group I from 0.19±0.21 to 0.44±0.33
Group II from 0.19±0.16 to 0.51±0.33
Mean DCVA change:
Group I from 0.58±0.30 to 0.62±0.24
Group II from 0.57±0.25 to 0.68±0.25
Myopic components were highly reduced (p<0.01)
Group I from −4.80±2.97 to −1.94±2.02
Group II from −4.65±2.23 to −2.22±2.47
Astigmatism was reduced in
Group I from 5.16±2.46 to −2.68±1.47
Group II from 4.60±0.83 to −3.60±1.40

FIG. 20A shows a chart of surgically induced astigmatism (SIA) vector versus target induced astigmatism (TIA) vector. FIG. 20B shows a chart of Cartesian astigmatism (J0) and oblique astigmatism (J45) both pre-surgery and post-surgery.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean (at least one of A, at least one of B, AND at least one of C). It should be understood that one or more steps within a method may be executed in different order (or concurrently) without altering the principles of the present disclosure.

In this application, including the definitions below, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory is a subset of the term computer-readable medium.

The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium include nonvolatile memory (such as flash memory), volatile memory (such as static random access memory and dynamic random access memory), magnetic storage (such as magnetic tape or hard disk drive), and optical storage.

The apparatuses and methods described in this application may be partially or fully implemented by one or more computer programs executed by one or more processors. The computer programs include processor-executable instructions that are stored on at least one non-transitory, tangible computer-readable medium. The computer programs may also include and/or rely on stored data.

Example Nomograms

Example specified nomograms according to the principles of the present disclosure are shown below in markup language format. MT (microns temporal) specifies the thickness of the temporal ICRS. DT (degrees temporal) specifies the arc angle of the temporal ICRS in degrees. MN (microns nasal) specifies the thickness of the nasal ICRS in degrees. DN (degrees nasal) specifies the arc angle of the nasal ICRS in degrees. Some or all of these specified nomograms may be unique to the present disclosure.

```
<nomograms>
<nomogram name="highkeratometric">
<item ESF="0/-2" CYL="0/-3">
    <plan Option="1" ring="in7" MT="300" DT="150" MN="300" DN="150"/>
</item>
<item ESF="0/-2" CYL="-3.01/-4">
    <plan Option="1" ring="sk6" MT="300" DT="130" MN="300" DN="130"/>
</item>
<item ESF="0/-2" CYL="-4.01/-6">
    <plan Option="1" ring="fr6" MT="150" DT="120" MN="150" DN="120"/>
</item>
<item ESF="-2.01/-3" CYL="0/-2">
    <plan Option="1" ring="in7" MT="300" DT="150" MN="300" DN="150"/>
</item>
<item ESF="-2.01/-3" CYL="-2.01/-4">
    <plan Option="1" ring="sk6" MT="300" DT="150" MN="300" DN="150"/>
</item>
<item ESF="-2.01/-3" CYL="-4.01/-6">
    <plan Option="1" ring="fr6" MT="150" DT="120" MN="150" DN="120"/>
</item>
<item ESF="-3.01/-4" CYL="0/-2">
    <plan Option="1" ring="in7" MT="350" DT="150" MN="350" DN="150"/>
</item>
<item ESF="-3.01/-4" CYL="-2.01/-4">
    <plan Option="1" ring="sk6" MT="350" DT="150" MN="350" DN="150"/>
</item>
<item ESF="-3.01/-4" CYL="-4.01/-6">
    <plan Option="1" ring="fr6" MT="150" DT="120" MN="150" DN="120"/>
</item>
<item ESF="-4.01/-5" CYL="0/-2">
    <plan Option="1" ring="in7" MT="400" DT="150" MN="400" DN="150"/>
</item>
<item ESF="-4.01/-5" CYL="-2.01/-4">
    <plan Option="1" ring="sk6" MT="400" DT="150" MN="400" DN="150"/>
</item>
<item ESF="-4.01/-5" CYL="-4.01/-6">
    <plan Option="1" ring="fr6" MT="150" DT="120" MN="150" DN="120"/>
</item>
<item ESF="-5.01/-6" CYL="0/-2">
    <plan Option="1" ring="in7" MT="450" DT="150" MN="450" DN="150"/>
</item>
<item ESF="-5.01/-6" CYL="-2.01/-4">
    <plan Option="1" ring="sk6" MT="450" DT="150" MN="450" DN="150"/>
</item>
<item ESF="-5.01/-6" CYL="-4.01/-6">
    <plan Option="1" ring="fr6" MT="150" DT="120" MN="150" DN="120"/>
</item>
<item ESF="-6.01/-7" CYL="0/-2">
```

```
    <plan Option="1" ring="sk6" MT="400" DT="150" MN="400" DN="150"/>
</item>
<item ESF="-6.01/-7" CYL="-2.01/-4">
    <plan Option="1" ring="sk6" MT="450" DT="150" MN="450" DN="150"/>
</item>
<item ESF="-6.01/-7" CYL="-4.01/-6">
    <plan Option="1" ring="fr6" MT="150" DT="140" MN="150" DN="140"/>
</item>
<item ESF="-7.01/-12" CYL="0/-2">
    <plan Option="1" ring="sk6" MT="450" DT="150" MN="450" DN="150"/>
</item>
<item ESF="-7.01/-12" CYL="-2.01/-4">
    <plan Option="1" ring="sk6" MT="450" DT="150" MN="450" DN="150"/>
</item>
<item ESF="-7.01/-12" CYL="-4.01/-6">
    <plan Option="1" ring="fr6" MT="150" DT="140" MN="150" DN="140"/>
</item>
<item ESF="-12.01/-15" CYL="0/-2">
    <plan Option="1" ring="sk6" MT="450" DT="150" MN="450" DN="150"/>
</item>
<item ESF="-12.01/-15" CYL="-2.01/-4">
    <plan Option="1" ring="sk6" MT="450" DT="150" MN="450" DN="150"/>
</item>
<item ESF="-12.01/-15" CYL="-4.01/-6">
    <plan Option="1" ring="fr6" MT="150" DT="140" MN="150" DN="140"/>
</item>
</nomogram>
<nomogram name="snowmannc">
<item ESF="-8/5" CYL="-1">
    <plan Option="1" ring="sk6" MT="300" DT="150" MN="250" DN="150"/>
    <plan Option="2" ring="in7" MT="350" DT="150" MN="350" DN="150"/>
</item>
<item ESF="-8/5" CYL="-2">
    <plan Option="1" ring="sk6" MT="300" DT="150" MN="250" DN="150"/>
</item>
<item ESF="-8/5" CYL="-3">
    <plan Option="1" ring="sk6" MT="400" DT="150" MN="400" DN="150"/>
    <plan Option="2" ring="frsk6" MT="150" DT="140" MN="300" DN="130"/>
</item>
<item ESF="-8/5" CYL="-4">
    <plan Option="1" ring="frsk6" MT="150" DT="140" MN="300" DN="130"/>
    <plan Option="2" ring="sk6" MT="400" DT="130" MN="400" DN="130"/>
</item>
<item ESF="-8/5" CYL="-8/-5">
    <plan Option="1" ring="frsk6" MT="150" DT="140" MN="300" DN="130"/>
    <plan Option="2" ring="fr6" MT="150" DT="140" MN="150" DN="90"/>
    <plan Option="3" ring="sk6" MT="400" DT="130" MN="400" DN="130"/>
</item>
</nomogram>
<nomogram name="asbowtie">
<item ESF="0/1" CYL="-3/-1">
    <plan Option="1" ring="sk6" MT="350" DT="130" MN="350" DN="130"/>
</item>
<item ESF="0/1" CYL="-5/-4">
    <plan Option="1" ring="fr6" MT="150" DT="90" MN="150" DN="90"/>
    <plan Option="2" ring="fr6" MT="150" DT="120" MN="150" DN="120"/>
</item>
<item ESF="0/1" CYL="-7/-6">
    <plan Option="1" ring="fr6" MT="150" DT="120" MN="150" DN="120"/>
    <plan Option="2" ring="fr5" MT="150" DT="120" MN="150" DN="120"/>
</item>
<item ESF="-3/1" CYL="-8">
    <plan Option="1" ring="fr6" MT="150" DT="120" MN="150" DN="120"/>
    <plan Option="2" ring="fr5" MT="150" DT="120" MN="150" DN="120"/>
</item>
<item ESF="-3/1" CYL="-9">
    <plan Option="1" ring="fr6" MT="150" DT="140" MN="150" DN="120"/>
    <plan Option="2" ring="fr5" MT="150" DT="120" MN="150" DN="120"/>
</item>
<item ESF="-3/1" CYL="-11/-10">
    <plan Option="1" ring="fr6" MT="150" DT="140" MN="150" DN="140"/>
    <plan Option="2" ring="fr5" MT="200" DT="120" MN="200" DN="120"/>
</item>
<item ESF="-1" CYL="-3/1">
    <plan Option="1" ring="fr6" MT="350" DT="130" MN="350" DN="130"/>
</item>
<item ESF="-1" CYL="-5/-4">
    <plan Option="1" ring="fr5" MT="150" DT="90" MN="150" DN="90"/>
    <plan Option="2" ring="fr6" MT="350" DT="130" MN="350" DN="130"/>
</item>
<item ESF="-1" CYL="-7/-6">
    <plan Option="1" ring="fr6" MT="150" DT="120" MN="150" DN="120"/>
    <plan Option="2" ring="fr6" MT="150" DT="120" MN="150" DN="90"/>
</item>
<item ESF="-2" CYL="-1">
    <plan Option="1" ring="sk6" MT="250" DT="130" MN="250" DN="130"/>
    <plan Option="2" ring="fr6" MT="150" DT="120" MN="0" DN="0"/>
</item>
<item ESF="-2" CYL="-2">
    <plan Option="1" ring="sk6" MT="350" DT="130" MN="350" DN="130"/>
    <plan Option="2" ring="fr6" MT="150" DT="120" MN="0" DN="0"/>
```

```
</item>
<item ESF="-2" CYL="-3">
  <plan Option="1" ring="sk6" MT="400" DT="130" MN="400" DN="130"/>
  <plan Option="2" ring="fr6" MT="150" DT="120" MN="0" DN="0"/>
</item>
<item ESF="-2" CYL="-4">
  <plan Option="1" ring="fr6" MT="150" DT="90" MN="150" DN="90"/>
  <plan Option="2" ring="sk6" MT="300" DT="150" MN="300" DN="150"/>
</item>
<item ESF="-2" CYL="-5">
  <plan Option="1" ring="fr6" MT="150" DT="90" MN="150" DN="90"/>
  <plan Option="2" ring="sk6" MT="300" DT="150" MN="300" DN="130"/>
</item>
<item ESF="-3/-2" CYL="-7/-6">
  <plan Option="1" ring="fr6" MT="150" DT="120" MN="150" DN="90"/>
  <plan Option="2" ring="fr6" MT="150" DT="120" MN="150" DN="120"/>
</item>
<item ESF="-3" CYL="-1">
  <plan Option="1" ring="sk6" MT="300" DT="150" MN="300" DN="150"/>
  <plan Option="2" ring="fr6" MT="150" DT="120" MN="0" DN="0"/>
</item>
<item ESF="-3" CYL="-2">
  <plan Option="1" ring="sk6" MT="350" DT="150" MN="350" DN="150"/>
  <plan Option="2" ring="fr6" MT="150" DT="120" MN="0" DN="0"/>
</item>
<item ESF="-3" CYL="-3">
  <plan Option="1" ring="sk6" MT="400" DT="150" MN="400" DN="150"/>
  <plan Option="2" ring="fr6" MT="150" DT="120" MN="0" DN="0"/>
</item>
<item ESF="-3" CYL="-4">
  <plan Option="1" ring="fr6" MT="150" DT="90" MN="150" DN="90"/>
  <plan Option="2" ring="sk6" MT="350" DT="150" MN="350" DN="150"/>
</item>
<item ESF="-3" CYL="-5">
  <plan Option="1" ring="fr6" MT="150" DT="90" MN="150" DN="90"/>
  <plan Option="2" ring="sk6" MT="300" DT="150" MN="300" DN="130"/>
</item>
<item ESF="-5/-4" CYL="-1">
  <plan Option="1" ring="sk6" MT="350" DT="150" MN="350" DN="150"/>
  <plan Option="2" ring="fr6" MT="150" DT="120" MN="0" DN="0"/>
</item>
<item ESF="-5/-4" CYL="-2">
  <plan Option="1" ring="sk6" MT="400" DT="150" MN="400" DN="150"/>
  <plan Option="2" ring="fr6" MT="150" DT="120" MN="0" DN="0"/>
</item>
<item ESF="-5/-4" CYL="-3">
  <plan Option="1" ring="sk6" MT="450" DT="150" MN="450" DN="150"/>
  <plan Option="2" ring="fr6" MT="150" DT="120" MN="0" DN="0"/>
</item>
<item ESF="-5/-4" CYL="-4">
  <plan Option="1" ring="fr6" MT="150" DT="120" MN="150" DN="120"/>
  <plan Option="2" ring="sk6" MT="400" DT="150" MN="400" DN="150"/>
</item>
<item ESF="-5/-4" CYL="-5">
  <plan Option="1" ring="fr6" MT="150" DT="120" MN="150" DN="120"/>
  <plan Option="2" ring="frsk6" MT="150" DT="120" MN="300" DN="120"/>
</item>
<item ESF="-4" CYL="-6">
  <plan Option="1" ring="fr6" MT="150" DT="140" MN="150" DN="140"/>
  <plan Option="2" ring="fr6" MT="150" DT="120" MN="150" DN="90"/>
</item>
<item ESF="-4" CYL="-7">
  <plan Option="1" ring="fr6" MT="200" DT="140" MN="200" DN="140"/>
  <plan Option="2" ring="fr6" MT="150" DT="120" MN="150" DN="90"/>
</item>
<item ESF="-4" CYL="-9/-8">
  <plan Option="1" ring="fr6" MT="200" DT="140" MN="200" DN="140"/>
  <plan Option="2" ring="fr5" MT="150" DT="120" MN="150" DN="120"/>
</item>
<item ESF="-4" CYL="-11/-10">
  <plan Option="1" ring="fr6" MT="150" DT="160" MN="150" DN="160"/>
  <plan Option="2" ring="fr5" MT="200" DT="120" MN="200" DN="120"/>
</item>
<item ESF="-9/-5" CYL="-7/-6">
  <plan Option="1" ring="fr6" MT="200" DT="140" MN="200" DN="140"/>
  <plan Option="2" ring="fr6" MT="150" DT="140" MN="150" DN="120"/>
</item>
<item ESF="-9/-5" CYL="-9/-8">
  <plan Option="1" ring="fr6" MT="200" DT="140" MN="200" DN="140"/>
  <plan Option="2" ring="fr5" MT="150" DT="140" MN="150" DN="140"/>
</item>
<item ESF="-9/-5" CYL="-11/-10">
  <plan Option="1" ring="fr6" MT="150" DT="160" MN="150" DN="160"/>
  <plan Option="2" ring="fr5" MT="200" DT="140" MN="200" DN="140"/>
</item>
<item ESF="-9/-6" CYL="-1">
  <plan Option="1" ring="sk6" MT="350" DT="150" MN="350" DN="150"/>
  <plan Option="2" ring="frsk6" MT="150" DT="120" MN="350" DN="150"/>
```

```xml
</item>
<item ESF="-9/-6" CYL="-2">
    <plan Option="1" ring="sk6" MT="400" DT="150" MN="400" DN="150"/>
    <plan Option="2" ring="frsk6" MT="150" DT="120" MN="350" DN="150"/>
</item>
<item ESF="-9/-6" CYL="-3">
    <plan Option="1" ring="sk6" MT="450" DT="150" MN="450" DN="150"/>
    <plan Option="2" ring="frsk6" MT="150" DT="120" MN="350" DN="150"/>
</item>
<item ESF="-9/-6" CYL="-4">
    <plan Option="1" ring="fr6" MT="150" DT="120" MN="150" DN="120"/>
    <plan Option="2" ring="sk6" MT="450" DT="150" MN="450" DN="120"/>
</item>
<item ESF="-9/-6" CYL="-5">
    <plan Option="1" ring="fr6" MT="150" DT="120" MN="150" DN="120"/>
    <plan Option="2" ring="frsk6" MT="200" DT="120" MN="350" DN="150"/>
</item>
</nomogram>
<nomogram name="asbowtieinv">
<item ESF="0/1" CYL="-3/-1">
    <plan Option="1" ring="sk6" MT="350" DT="130" MN="350" DN="130"/>
</item>
<item ESF="0/1" CYL="-5/-4">
    <plan Option="1" ring="fr6" MT="150" DT="90" MN="150" DN="90"/>
    <plan Option="2" ring="fr6" MT="150" DT="120" MN="150" DN="120"/>
</item>
<item ESF="0/1" CYL="-7/-6">
    <plan Option="1" ring="fr6" MT="150" DT="120" MN="150" DN="120"/>
    <plan Option="2" ring="fr5" MT="150" DT="120" MN="150" DN="120"/>
</item>
<item ESF="-3/1" CYL="-8">
    <plan Option="1" ring="fr6" MT="150" DT="120" MN="150" DN="120"/>
    <plan Option="2" ring="fr5" MT="150" DT="120" MN="150" DN="120"/>
</item>
<item ESF="-3/1" CYL="-9">
    <plan Option="1" ring="fr6" MT="150" DT="140" MN="150" DN="120"/>
    <plan Option="2" ring="fr5" MT="150" DT="120" MN="150" DN="120"/>
</item>
<item ESF="-3/1" CYL="-11/-10">
    <plan Option="1" ring="fr6" MT="150" DT="140" MN="150" DN="140"/>
    <plan Option="2" ring="fr5" MT="200" DT="120" MN="200" DN="120"/>
</item>
<item ESF="-1" CYL="-3/1">
    <plan Option="1" ring="fr6" MT="350" DT="130" MN="350" DN="130"/>
</item>
<item ESF="-1" CYL="-5/-4">
    <plan Option="1" ring="fr5" MT="150" DT="90" MN="150" DN="90"/>
    <plan Option="2" ring="fr6" MT="350" DT="130" MN="350" DN="130"/>
</item>
<item ESF="-1" CYL="-7/-6">
    <plan Option="1" ring="fr6" MT="150" DT="120" MN="150" DN="120"/>
    <plan Option="2" ring="fr6" MT="150" DT="120" MN="150" DN="90"/>
</item>
<item ESF="-2" CYL="-1">
    <plan Option="1" ring="sk6" MT="250" DT="130" MN="250" DN="130"/>
    <plan Option="2" ring="fr6" MT="150" DT="120" MN="0" DN="0"/>
</item>
<item ESF="-2" CYL="-2">
    <plan Option="1" ring="sk6" MT="350" DT="130" MN="350" DN="130"/>
    <plan Option="2" ring="fr6" MT="150" DT="120" MN="0" DN="0"/>
</item>
<item ESF="-2" CYL="-3">
    <plan Option="1" ring="sk6" MT="400" DT="130" MN="400" DN="130"/>
    <plan Option="2" ring="fr6" MT="150" DT="120" MN="0" DN="0"/>
</item>
<item ESF="-2" CYL="-4">
    <plan Option="1" ring="fr6" MT="150" DT="90" MN="150" DN="90"/>
    <plan Option="2" ring="sk6" MT="300" DT="150" MN="300" DN="150"/>
</item>
<item ESF="-2" CYL="-5">
    <plan Option="1" ring="fr6" MT="150" DT="90" MN="150" DN="90"/>
    <plan Option="2" ring="sk6" MT="300" DT="150" MN="300" DN="130"/>
</item>
<item ESF="-3/-2" CYL="-7/-6">
    <plan Option="1" ring="fr6" MT="150" DT="120" MN="150" DN="90"/>
    <plan Option="2" ring="fr6" MT="150" DT="120" MN="150" DN="120"/>
</item>
<item ESF="-3" CYL="-1">
    <plan Option="1" ring="sk6" MT="300" DT="150" MN="300" DN="150"/>
    <plan Option="2" ring="fr6" MT="150" DT="120" MN="0" DN="0"/>
</item>
<item ESF="-3" CYL="-2">
    <plan Option="1" ring="sk6" MT="350" DT="150" MN="350" DN="150"/>
    <plan Option="2" ring="fr6" MT="150" DT="120" MN="0" DN="0"/>
</item>
<item ESF="-3" CYL="-3">
    <plan Option="1" ring="sk6" MT="400" DT="150" MN="400" DN="150"/>
    <plan Option="2" ring="fr6" MT="150" DT="120" MN="0" DN="0"/>
```

```xml
</item>
<item ESF="-3" CYL="-4">
  <plan Option="1" ring="fr6" MT="150" DT="90" MN="150" DN="90"/>
  <plan Option="2" ring="sk6" MT="350" DT="150" MN="350" DN="150"/>
</item>
<item ESF="-3" CYL="-5">
  <plan Option="1" ring="fr6" MT="150" DT="90" MN="150" DN="90"/>
  <plan Option="2" ring="sk6" MT="300" DT="150" MN="300" DN="130"/>
</item>
<item ESF="-5/-4" CYL="-1">
  <plan Option="1" ring="sk6" MT="350" DT="150" MN="350" DN="150"/>
  <plan Option="2" ring="fr6" MT="150" DT="120" MN="0" DN="0"/>
</item>
<item ESF="-5/-4" CYL="-2">
  <plan Option="1" ring="sk6" MT="400" DT="150" MN="400" DN="150"/>
  <plan Option="2" ring="fr6" MT="150" DT="120" MN="0" DN="0"/>
</item>
<item ESF="-5/-4" CYL="-3">
  <plan Option="1" ring="sk6" MT="450" DT="150" MN="450" DN="150"/>
  <plan Option="2" ring="fr6" MT="150" DT="120" MN="0" DN="0"/>
</item>
<item ESF="-5/-4" CYL="-4">
  <plan Option="1" ring="fr6" MT="150" DT="120" MN="150" DN="120"/>
  <plan Option="2" ring="sk6" MT="400" DT="150" MN="400" DN="150"/>
</item>
<item ESF="-5/-4" CYL="-5">
  <plan Option="1" ring="fr6" MT="150" DT="120" MN="150" DN="120"/>
  <plan Option="2" ring="frsk6" MT="150" DT="120" MN="300" DN="120"/>
</item>
<item ESF="-4" CYL="-6">
  <plan Option="1" ring="fr6" MT="150" DT="140" MN="150" DN="140"/>
  <plan Option="2" ring="fr6" MT="150" DT="120" MN="150" DN="90"/>
</item>
<item ESF="-4" CYL="-7">
  <plan Option="1" ring="fr6" MT="200" DT="140" MN="200" DN="140"/>
  <plan Option="2" ring="fr6" MT="150" DT="120" MN="150" DN="90"/>
</item>
<item ESF="-4" CYL="-9/-8">
  <plan Option="1" ring="fr6" MT="200" DT="140" MN="200" DN="140"/>
  <plan Option="2" ring="fr5" MT="150" DT="120" MN="150" DN="120"/>
</item>
<item ESF="-4" CYL="-11/-10">
  <plan Option="1" ring="fr6" MT="150" DT="160" MN="150" DN="160"/>
  <plan Option="2" ring="fr5" MT="200" DT="120" MN="200" DN="120"/>
</item>
<item ESF="-9/-5" CYL="-7/-6">
  <plan Option="1" ring="fr6" MT="200" DT="140" MN="200" DN="140"/>
  <plan Option="2" ring="fr6" MT="150" DT="140" MN="150" DN="120"/>
</item>
<item ESF="-9/-5" CYL="-9/-8">
  <plan Option="1" ring="fr6" MT="200" DT="140" MN="200" DN="140"/>
  <plan Option="2" ring="fr5" MT="150" DT="140" MN="150" DN="140"/>
</item>
<item ESF="-9/-5" CYL="-11/-10">
  <plan Option="1" ring="fr6" MT="150" DT="160" MN="150" DN="160"/>
  <plan Option="2" ring="fr5" MT="200" DT="140" MN="200" DN="140"/>
</item>
<item ESF="-9/-6" CYL="-1">
  <plan Option="1" ring="sk6" MT="350" DT="150" MN="350" DN="150"/>
  <plan Option="2" ring="frsk6" MT="150" DT="120" MN="350" DN="150"/>
</item>
<item ESF="-9/-6" CYL="-2">
  <plan Option="1" ring="sk6" MT="400" DT="150" MN="400" DN="150"/>
  <plan Option="2" ring="frsk6" MT="150" DT="120" MN="350" DN="150"/>
</item>
<item ESF="-9/-6" CYL="-3">
  <plan Option="1" ring="sk6" MT="450" DT="150" MN="450" DN="150"/>
  <plan Option="2" ring="frsk6" MT="150" DT="120" MN="350" DN="150"/>
</item>
<item ESF="-9/-6" CYL="-4">
  <plan Option="1" ring="fr6" MT="150" DT="120" MN="150" DN="120"/>
  <plan Option="2" ring="sk6" MT="450" DT="150" MN="450" DN="120"/>
</item>
<item ESF="-9/-6" CYL="-5">
  <plan Option="1" ring="fr6" MT="150" DT="120" MN="150" DN="120"/>
  <plan Option="2" ring="frsk6" MT="200" DT="120" MN="350" DN="150"/>
</item>
</nomogram>
<nomogram name="smbowtie">
<item ESF="0/1" CYL="-3/-1">
  <plan Option="1" ring="sk6" MT="350" DT="130" MN="350" DN="130"/>
</item>
<item ESF="0/1" CYL="-5/-4">
  <plan Option="1" ring="fr6" MT="150" DT="90" MN="150" DN="90"/>
  <plan Option="2" ring="fr6" MT="150" DT="120" MN="150" DN="120"/>
</item>
<item ESF="0/1" CYL="-7/-6">
  <plan Option="1" ring="fr6" MT="150" DT="120" MN="150" DN="120"/>
  <plan Option="2" ring="fr5" MT="150" DT="120" MN="150" DN="120"/>
```

```
</item>
<item ESF="-3/1" CYL="-8">
  <plan Option="1" ring="fr6" MT="150" DT="120" MN="150" DN="120"/>
  <plan Option="2" ring="fr5" MT="150" DT="120" MN="150" DN="120"/>
</item>
<item ESF="-3/1" CYL="-9">
  <plan Option="1" ring="fr6" MT="150" DT="140" MN="150" DN="120"/>
  <plan Option="2" ring="fr5" MT="150" DT="120" MN="150" DN="120"/>
</item>
<item ESF="-3/1" CYL="-11/-10">
  <plan Option="1" ring="fr6" MT="150" DT="140" MN="150" DN="140"/>
  <plan Option="2" ring="fr5" MT="200" DT="120" MN="200" DN="120"/>
</item>
<item ESF="-1" CYL="-3/1">
  <plan Option="1" ring="sk6" MT="350" DT="130" MN="350" DN="130"/>
</item>
<item ESF="-1" CYL="-5/-4">
  <plan Option="1" ring="fr5" MT="150" DT="90" MN="150" DN="90"/>
  <plan Option="2" ring="sk6" MT="350" DT="130" MN="350" DN="130"/>
</item>
<item ESF="-1" CYL="-7/-6">
  <plan Option="1" ring="fr5" MT="150" DT="120" MN="150" DN="120"/>
  <plan Option="2" ring="fr6" MT="150" DT="120" MN="150" DN="90"/>
</item>
<item ESF="-2" CYL="-1">
  <plan Option="1" ring="sk6" MT="250" DT="130" MN="250" DN="130"/>
  <plan Option="2" ring="fr6" MT="150" DT="120" MN="0" DN="0"/>
</item>
<item ESF="-2" CYL="-2">
  <plan Option="1" ring="sk6" MT="350" DT="130" MN="350" DN="130"/>
  <plan Option="2" ring="fr6" MT="150" DT="120" MN="0" DN="0"/>
</item>
<item ESF="-2" CYL="-3">
  <plan Option="1" ring="sk6" MT="400" DT="130" MN="400" DN="130"/>
  <plan Option="2" ring="fr6" MT="150" DT="120" MN="0" DN="0"/>
</item>
<item ESF="-2" CYL="-4">
  <plan Option="1" ring="fr6" MT="150" DT="90" MN="150" DN="90"/>
  <plan Option="2" ring="sk6" MT="300" DT="150" MN="300" DN="150"/>
</item>
<item ESF="-2" CYL="-5">
  <plan Option="1" ring="fr6" MT="150" DT="90" MN="150" DN="90"/>
  <plan Option="2" ring="sk6" MT="300" DT="150" MN="300" DN="130"/>
</item>
<item ESF="-3/-2" CYL="-7/-6">
  <plan Option="1" ring="fr6" MT="150" DT="120" MN="150" DN="90"/>
  <plan Option="2" ring="fr6" MT="150" DT="120" MN="150" DN="120"/>
</item>
<item ESF="-3" CYL="-1">
  <plan Option="1" ring="sk6" MT="300" DT="150" MN="300" DN="150"/>
  <plan Option="2" ring="fr6" MT="150" DT="120" MN="0" DN="0"/>
</item>
<item ESF="-3" CYL="-2">
  <plan Option="1" ring="sk6" MT="350" DT="150" MN="350" DN="150"/>
  <plan Option="2" ring="fr6" MT="150" DT="120" MN="0" DN="0"/>
</item>
<item ESF="-3" CYL="-3">
  <plan Option="1" ring="sk6" MT="400" DT="150" MN="400" DN="150"/>
  <plan Option="2" ring="fr6" MT="150" DT="120" MN="0" DN="0"/>
</item>
<item ESF="-3" CYL="-4">
  <plan Option="1" ring="fr6" MT="150" DT="90" MN="150" DN="90"/>
  <plan Option="2" ring="sk6" MT="350" DT="150" MN="350" DN="150"/>
</item>
<item ESF="-3" CYL="-5">
  <plan Option="1" ring="fr6" MT="150" DT="90" MN="150" DN="90"/>
  <plan Option="2" ring="sk6" MT="300" DT="150" MN="300" DN="130"/>
</item>
<item ESF="-5/-4" CYL="-1">
  <plan Option="1" ring="sk6" MT="350" DT="150" MN="350" DN="150"/>
  <plan Option="2" ring="fr6" MT="150" DT="120" MN="0" DN="0"/>
</item>
<item ESF="-5/-4" CYL="-2">
  <plan Option="1" ring="sk6" MT="400" DT="150" MN="400" DN="150"/>
  <plan Option="2" ring="fr6" MT="150" DT="120" MN="0" DN="0"/>
</item>
<item ESF="-5/-4" CYL="-3">
  <plan Option="1" ring="sk6" MT="450" DT="150" MN="450" DN="150"/>
  <plan Option="2" ring="fr6" MT="150" DT="120" MN="0" DN="0"/>
</item>
<item ESF="-5/-4" CYL="-4">
  <plan Option="1" ring="fr6" MT="150" DT="120" MN="150" DN="120"/>
  <plan Option="2" ring="sk6" MT="400" DT="150" MN="400" DN="150"/>
</item>
<item ESF="-5/-4" CYL="-5">
  <plan Option="1" ring="fr6" MT="150" DT="120" MN="150" DN="120"/>
  <plan Option="2" ring="frsk6" MT="150" DT="120" MN="300" DN="120"/>
</item>
<item ESF="-4" CYL="-6">
  <plan Option="1" ring="fr6" MT="150" DT="140" MN="150" DN="140"/>
```

```xml
    <plan Option="2" ring="fr6" MT="150" DT="120" MN="150" DN="90"/>
</item>
<item ESF="-4" CYL="-7">
    <plan Option="1" ring="fr6" MT="200" DT="140" MN="200" DN="140"/>
    <plan Option="2" ring="fr6" MT="150" DT="120" MN="150" DN="90"/>
</item>
<item ESF="-4" CYL="-9/-8">
    <plan Option="1" ring="fr6" MT="200" DT="140" MN="200" DN="140"/>
    <plan Option="2" ring="fr5" MT="150" DT="120" MN="150" DN="120"/>
</item>
<item ESF="-4" CYL="-11/-10">
    <plan Option="1" ring="fr6" MT="150" DT="160" MN="150" DN="160"/>
    <plan Option="2" ring="fr5" MT="200" DT="120" MN="200" DN="120"/>
</item>
<item ESF="-9/-5" CYL="-7/-6">
    <plan Option="1" ring="fr6" MT="200" DT="140" MN="200" DN="140"/>
    <plan Option="2" ring="fr6" MT="150" DT="140" MN="150" DN="120"/>
</item>
<item ESF="-9/-5" CYL="-9/-8">
    <plan Option="1" ring="fr6" MT="200" DT="140" MN="200" DN="140"/>
    <plan Option="2" ring="fr5" MT="150" DT="140" MN="150" DN="140"/>
</item>
<item ESF="-9/-5" CYL="-11/-10">
    <plan Option="1" ring="fr6" MT="150" DT="160" MN="150" DN="160"/>
    <plan Option="2" ring="fr5" MT="200" DT="140" MN="200" DN="140"/>
</item>
<item ESF="-9/-6" CYL="-1">
    <plan Option="1" ring="sk6" MT="350" DT="150" MN="350" DN="150"/>
    <plan Option="2" ring="frsk6" MT="150" DT="120" MN="350" DN="150"/>
</item>
<item ESF="-9/-6" CYL="-2">
    <plan Option="1" ring="sk6" MT="400" DT="150" MN="400" DN="150"/>
    <plan Option="2" ring="frsk6" MT="150" DT="120" MN="350" DN="150"/>
</item>
<item ESF="-9/-6" CYL="-3">
    <plan Option="1" ring="sk6" MT="450" DT="150" MN="450" DN="150"/>
    <plan Option="2" ring="frsk6" MT="150" DT="120" MN="350" DN="150"/>
</item>
<item ESF="-9/-6" CYL="-4">
    <plan Option="1" ring="fr6" MT="150" DT="120" MN="150" DN="120"/>
    <plan Option="2" ring="sk6" MT="450" DT="150" MN="450" DN="120"/>
</item>
<item ESF="-9/-6" CYL="-5">
    <plan Option="1" ring="fr6" MT="150" DT="120" MN="150" DN="120"/>
    <plan Option="2" ring="frsk6" MT="200" DT="120" MN="350" DN="150"/>
</item>
</nomogram>
<nomogram name="Igbowtie">
<item ESF="0/1" CYL="-3/-1">
    <plan Option="1" ring="sk6" MT="350" DT="130" MN="350" DN="130"/>
</item>
<item ESF="0/1" CYL="-5/-4">
    <plan Option="1" ring="fr6" MT="150" DT="90" MN="150" DN="90"/>
    <plan Option="2" ring="fr6" MT="150" DT="120" MN="150" DN="120"/>
</item>
<item ESF="0/1" CYL="-7/-6">
    <plan Option="1" ring="fr6" MT="150" DT="120" MN="150" DN="120"/>
    <plan Option="2" ring="fr5" MT="150" DT="120" MN="150" DN="120"/>
</item>
<item ESF="-3/1" CYL="-8">
    <plan Option="1" ring="fr6" MT="150" DT="120" MN="150" DN="120"/>
    <plan Option="2" ring="fr5" MT="150" DT="120" MN="150" DN="120"/>
</item>
<item ESF="-3/1" CYL="-9">
    <plan Option="1" ring="fr6" MT="150" DT="140" MN="150" DN="120"/>
    <plan Option="2" ring="fr5" MT="150" DT="120" MN="150" DN="120"/>
</item>
<item ESF="-3/1" CYL="-11/-10">
    <plan Option="1" ring="fr6" MT="150" DT="140" MN="150" DN="140"/>
    <plan Option="2" ring="fr5" MT="200" DT="120" MN="200" DN="120"/>
</item>
<item ESF="-1" CYL="-3/1">
    <plan Option="1" ring="fr6" MT="350" DT="130" MN="350" DN="130"/>
</item>
<item ESF="-1" CYL="-5/-4">
    <plan Option="1" ring="fr5" MT="150" DT="90" MN="150" DN="90"/>
    <plan Option="2" ring="fr6" MT="350" DT="130" MN="350" DN="130"/>
</item>
<item ESF="-1" CYL="-7/-6">
    <plan Option="1" ring="fr6" MT="150" DT="120" MN="150" DN="120"/>
    <plan Option="2" ring="fr6" MT="150" DT="120" MN="150" DN="90"/>
</item>
<item ESF="-2" CYL="-1">
    <plan Option="1" ring="sk6" MT="250" DT="130" MN="250" DN="130"/>
    <plan Option="2" ring="fr6" MT="150" DT="120" MN="0" DN="0"/>
</item>
<item ESF="-2" CYL="-2">
    <plan Option="1" ring="sk6" MT="350" DT="130" MN="350" DN="130"/>
    <plan Option="2" ring="fr6" MT="150" DT="120" MN="0" DN="0"/>
```

```xml
</item>
<item ESF="-2" CYL="-3">
  <plan Option="1" ring="sk6" MT="400" DT="130" MN="400" DN="130"/>
  <plan Option="2" ring="fr6" MT="150" DT="120" MN="0" DN="0"/>
<item ESF="-2" CYL="-4">
  <plan Option="1" ring="fr6" MT="150" DT="90" MN="150" DN="90"/>
  <plan Option="2" ring="sk6" MT="300" DT="150" MN="300" DN="150"/>
</item>
<item ESF="-2" CYL="-5">
  <plan Option="1" ring="fr6" MT="150" DT="90" MN="150" DN="90"/>
  <plan Option="2" ring="sk6" MT="300" DT="150" MN="300" DN="130"/>
</item>
<item ESF="-3/-2" CYL="-7/-6">
  <plan Option="1" ring="fr6" MT="150" DT="120" MN="150" DN="90"/>
  <plan Option="2" ring="fr6" MT="150" DT="120" MN="150" DN="120"/>
</item>
<item ESF="-3" CYL="-1">
  <plan Option="1" ring="sk6" MT="300" DT="150" MN="300" DN="150"/>
  <plan Option="2" ring="fr6" MT="150" DT="120" MN="0" DN="0"/>
</item>
<item ESF="-3" CYL="-2">
  <plan Option="1" ring="sk6" MT="350" DT="150" MN="350" DN="150"/>
  <plan Option="2" ring="fr6" MT="150" DT="120" MN="0" DN="0"/>
</item>
<item ESF="-3" CYL="-3">
  <plan Option="1" ring="sk6" MT="400" DT="150" MN="400" DN="150"/>
  <plan Option="2" ring="fr6" MT="150" DT="120" MN="0" DN="0"/>
</item>
<item ESF="-3" CYL="-4">
  <plan Option="1" ring="fr6" MT="150" DT="90" MN="150" DN="90"/>
  <plan Option="2" ring="sk6" MT="350" DT="150" MN="350" DN="150"/>
</item>
<item ESF="-3" CYL="-5">
  <plan Option="1" ring="fr6" MT="150" DT="90" MN="150" DN="90"/>
  <plan Option="2" ring="sk6" MT="300" DT="150" MN="300" DN="130"/>
</item>
<item ESF="-5/-4" CYL="-1">
  <plan Option="1" ring="sk6" MT="350" DT="150" MN="350" DN="150"/>
  <plan Option="2" ring="fr6" MT="150" DT="120" MN="0" DN="0"/>
</item>
<item ESF="-5/-4" CYL="-2">
  <plan Option="1" ring="sk6" MT="400" DT="150" MN="400" DN="150"/>
  <plan Option="2" ring="fr6" MT="150" DT="120" MN="0" DN="0"/>
</item>
<item ESF="-5/-4" CYL="-3">
  <plan Option="1" ring="sk6" MT="450" DT="150" MN="450" DN="150"/>
  <plan Option="2" ring="fr6" MT="150" DT="120" MN="0" DN="0"/>
</item>
<item ESF="-5/-4" CYL="-4">
  <plan Option="1" ring="fr6" MT="150" DT="120" MN="150" DN="120"/>
  <plan Option="2" ring="sk6" MT="400" DT="150" MN="400" DN="150"/>
</item>
<item ESF="-5/-4" CYL="-5">
  <plan Option="1" ring="fr6" MT="150" DT="120" MN="150" DN="120"/>
  <plan Option="2" ring="frsk6" MT="150" DT="120" MN="300" DN="120"/>
</item>
<item ESF="-4" CYL="-6">
  <plan Option="1" ring="fr6" MT="150" DT="140" MN="150" DN="140"/>
  <plan Option="2" ring="fr6" MT="150" DT="120" MN="150" DN="90"/>
</item>
<item ESF="-4" CYL="-7">
  <plan Option="1" ring="fr6" MT="200" DT="140" MN="200" DN="140"/>
  <plan Option="2" ring="fr6" MT="150" DT="120" MN="150" DN="90"/>
</item>
<item ESF="-4" CYL="-9/-8">
  <plan Option="1" ring="fr6" MT="200" DT="140" MN="200" DN="140"/>
  <plan Option="2" ring="fr5" MT="150" DT="120" MN="150" DN="120"/>
</item>
<item ESF="-4" CYL="-11/-10">
  <plan Option="1" ring="fr6" MT="150" DT="160" MN="150" DN="160"/>
  <plan Option="2" ring="fr5" MT="200" DT="120" MN="200" DN="120"/>
</item>
<item ESF="-9/-5" CYL="-7/-6">
  <plan Option="1" ring="fr6" MT="200" DT="140" MN="200" DN="140"/>
  <plan Option="2" ring="fr6" MT="150" DT="140" MN="150" DN="120"/>
</item>
<item ESF="-9/-5" CYL="-9/-8">
  <plan Option="1" ring="fr6" MT="200" DT="140" MN="200" DN="140"/>
  <plan Option="2" ring="fr5" MT="150" DT="140" MN="150" DN="140"/>
</item>
<item ESF="-9/-5" CYL="-11/-10">
  <plan Option="1" ring="fr6" MT="150" DT="160" MN="150" DN="160"/>
  <plan Option="2" ring="fr5" MT="200" DT="140" MN="200" DN="140"/>
</item>
<item ESF="-9/-6" CYL="-1">
  <plan Option="1" ring="sk6" MT="350" DT="150" MN="350" DN="150"/>
  <plan Option="2" ring="frsk6" MT="150" DT="120" MN="350" DN="150"/>
```

```
</item>
<item ESF="-9/-6" CYL="-2">
  <plan Option="1" ring="sk6" MT="400" DT="150" MN="400" DN="150"/>
  <plan Option="2" ring="frsk6" MT="150" DT="120" MN="350" DN="150"/>
</item>
<item ESF="-9/-6" CYL="-3">
  <plan Option="1" ring="sk6" MT="450" DT="150" MN="450" DN="150"/>
  <plan Option="2" ring="frsk6" MT="150" DT="120" MN="350" DN="150"/>
</item>
<item ESF="-9/-6" CYL="-4">
  <plan Option="1" ring="fr6" MT="150" DT="120" MN="150" DN="120"/>
  <plan Option="2" ring="sk6" MT="450" DT="150" MN="450" DN="120"/>
</item>
<item ESF="-9/-6" CYL="-5">
  <plan Option="1" ring="fr6" MT="150" DT="120" MN="150" DN="120"/>
  <plan Option="2" ring="frsk6" MT="200" DT="120" MN="350" DN="150"/>
</item>
</nomogram>
<nomogram name="snowman">
<item ESF="1" CYL="0/1">
  <plan Option="1" ring="sk6" MT="250" DT="130" MN="250" DN="130"/>
  <plan Option="2" ring="frsk6" MT="150" DT="90" MN="250" DN="130"/>
</item>
<item ESF="0" CYL="1">
  <plan Option="1" ring="sk6" MT="250" DT="130" MN="250" DN="130"/>
  <plan Option="2" ring="frsk6" MT="150" DT="90" MN="250" DN="130"/>
</item>
<item ESF="2" CYL="-1/0">
  <plan Option="1" ring="sk6" MT="250" DT="130" MN="250" DN="130"/>
  <plan Option="2" ring="frsk6" MT="150" DT="90" MN="250" DN="130"/>
</item>
<item ESF="2/1" CYL="-3/-2">
  <plan Option="1" ring="sk6" MT="300" DT="130" MN="300" DN="130"/>
  <plan Option="2" ring="sk6" MT="350" DT="130" MN="350" DN="130"/>
</item>
<item ESF="0/1" CYL="-1">
  <plan Option="1" ring="sk6" MT="250" DT="130" MN="250" DN="130"/>
  <plan Option="2" ring="sk6" MT="300" DT="130" MN="300" DN="130"/>
</item>
<item ESF="0" CYL="-2">
  <plan Option="1" ring="sk6" MT="300" DT="130" MN="300" DN="130"/>
  <plan Option="2" ring="sk6" MT="350" DT="130" MN="350" DN="130"/>
</item>
<item ESF="0" CYL="-3">
  <plan Option="1" ring="sk6" MT="350" DT="130" MN="350" DN="130"/>
  <plan Option="2" ring="frsk6" MT="150" DT="120" MN="300" DN="130"/>
</item>
<item ESF="-1" CYL="-3">
  <plan Option="1" ring="frsk6" MT="150" DT="90" MN="350" DN="130"/>
  <plan Option="2" ring="frsk6" MT="150" DT="120" MN="300" DN="130"/>
</item>
<item ESF="-1" CYL="0/2">
  <plan Option="1" ring="in7" MT="250" DT="150" MN="250" DN="150"/>
  <plan Option="2" ring="sk6" MT="210" DT="150" MN="210" DN="150"/>
</item>
<item ESF="-1/2" CYL="-2/-1">
  <plan Option="1" ring="sk6" MT="300" DT="130" MN="300" DN="130"/>
  <plan Option="2" ring="frsk6" MT="150" DT="90" MN="300" DN="130"/>
</item>
<item ESF="-1/2" CYL="-6/-4">
  <plan Option="1" ring="fr6" MT="150" DT="90" MN="150" DN="90"/>
  <plan Option="2" ring="frsk6" MT="150" DT="120" MN="300" DN="150"/>
</item>
<item ESF="-2" CYL="-2/-1">
  <plan Option="1" ring="sk6" MT="350" DT="130" MN="350" DN="130"/>
  <plan Option="2" ring="frsk6" MT="150" DT="90" MN="300" DN="130"/>
</item>
<item ESF="-2" CYL="0/-2">
  <plan Option="1" ring="in7" MT="300" DT="150" MN="300" DN="150"/>
  <plan Option="2" ring="sk6" MT="250" DT="150" MN="250" DN="150"/>
</item>
<item ESF="-3" CYL="0/-2">
  <plan Option="1" ring="in7" MT="350" DT="150" MN="350" DN="150"/>
  <plan Option="2" ring="sk6" MT="300" DT="150" MN="300" DN="150"/>
</item>
<item ESF="-4" CYL="0/-2">
  <plan Option="1" ring="in7" MT="400" DT="150" MN="400" DN="150"/>
  <plan Option="2" ring="sk6" MT="350" DT="150" MN="350" DN="150"/>
</item>
<item ESF="-5" CYL="0/-2">
  <plan Option="1" ring="in7" MT="450" DT="150" MN="450" DN="150"/>
  <plan Option="2" ring="sk6" MT="400" DT="150" MN="400" DN="150"/>
</item>
<item ESF="-6" CYL="0/-2">
  <plan Option="1" ring="sk6" MT="400" DT="150" MN="400" DN="150"/>
  <plan Option="2" ring="in7" MT="450" DT="150" MN="450" DN="150"/>
</item>
<item ESF="-8/-7" CYL="0/-2">
  <plan Option="1" ring="sk6" MT="450" DT="150" MN="450" DN="150"/>
```

```xml
    <plan Option="2" ring="in7" MT="450" DT="150" MN="450" DN="150"/>
</item>
<item ESF="-3" CYL="-2/-1">
    <plan Option="1" ring="sk6" MT="350" DT="130" MN="350" DN="130"/>
    <plan Option="2" ring="frsk6" MT="150" DT="90" MN="350" DN="150"/>
</item>
<item ESF="-4" CYL="-2/-1">
    <plan Option="1" ring="sk6" MT="400" DT="130" MN="400" DN="130"/>
    <plan Option="2" ring="frsk6" MT="150" DT="90" MN="350" DN="150"/>
</item>
<item ESF="-5" CYL="-1">
    <plan Option="1" ring="sk6" MT="400" DT="130" MN="400" DN="130"/>
    <plan Option="2" ring="frsk6" MT="150" DT="90" MN="400" DN="150"/>
</item>
<item ESF="-6/-5" CYL="-2">
    <plan Option="1" ring="sk6" MT="400" DT="150" MN="400" DN="150"/>
    <plan Option="2" ring="frsk6" MT="150" DT="90" MN="400" DN="150"/>
</item>
<item ESF="-6" CYL="-1">
    <plan Option="1" ring="sk6" MT="450" DT="130" MN="450" DN="130"/>
    <plan Option="2" ring="frsk6" MT="150" DT="90" MN="400" DN="150"/>
</item>
<item ESF="-8/-7" CYL="-2/-1">
    <plan Option="1" ring="sk6" MT="450" DT="130" MN="450" DN="130"/>
    <plan Option="2" ring="frsk6" MT="150" DT="90" MN="400" DN="150"/>
</item>
<item ESF="-4/-3" CYL="-4/-3">
    <plan Option="1" ring="frsk6" MT="150" DT="90" MN="350" DN="130"/>
    <plan Option="2" ring="frsk6" MT="150" DT="90" MN="350" DN="130"/>
</item>
<item ESF="-2" CYL="-4/-3">
    <plan Option="1" ring="frsk6" MT="150" DT="90" MN="350" DN="130"/>
    <plan Option="2" ring="frsk6" MT="150" DT="120" MN="300" DN="130"/>
</item>
<item ESF="-4/-2" CYL="-6/-5">
    <plan Option="1" ring="fr6" MT="150" DT="90" MN="150" DN="90"/>
    <plan Option="2" ring="frsk6" MT="200" DT="120" MN="350" DN="130"/>
</item>
<item ESF="-8/-5" CYL="-4/-3">
    <plan Option="1" ring="frsk6" MT="150" DT="90" MN="350" DN="130"/>
    <plan Option="2" ring="frsk6" MT="150" DT="120" MN="400" DN="130"/>
</item>
<item ESF="-8/-5" CYL="-6/-5">
    <plan Option="1" ring="fr6" MT="150" DT="90" MN="150" DN="90"/>
    <plan Option="2" ring="frsk6" MT="200" DT="120" MN="400" DN="130"/>
</item>
</nomogram>
<nomogram name="smallnipple">
<item ESF="-1/3" CYL="-5/5">
    <plan Option="1" ring="kr5355" MT="150" DT="355" MN="0" DN="0"/>
    <plan Option="2" ring="fr6210" MT="150" DT="210" MN="0" DN="0"/>
    <plan Option="3" ring="in7" MT="300" DT="150" MN="300" DN="150"/>
</item>
<item ESF="-2" CYL="-5/5">
    <plan Option="1" ring="kr5355" MT="150" DT="355" MN="0" DN="0"/>
    <plan Option="2" ring="fr6210" MT="150" DT="210" MN="0" DN="0"/>
    <plan Option="3" ring="in7" MT="350" DT="150" MN="350" DN="150"/>
</item>
<item ESF="-3" CYL="-5/5">
    <plan Option="1" ring="kr5355" MT="200" DT="355" MN="0" DN="0"/>
    <plan Option="2" ring="fr6210" MT="200" DT="210" MN="0" DN="0"/>
    <plan Option="3" ring="in7" MT="400" DT="150" MN="400" DN="150"/>
</item>
<item ESF="-4" CYL="-5/5">
    <plan Option="1" ring="kr5355" MT="200" DT="355" MN="0" DN="0"/>
    <plan Option="2" ring="fr6210" MT="200" DT="210" MN="0" DN="0"/>
    <plan Option="3" ring="sk6" MT="350" DT="150" MN="350" DN="150"/>
</item>
<item ESF="-8/-5" CYL="-5/5">
    <plan Option="1" ring="kr5355" MT="200" DT="355" MN="0" DN="0"/>
    <plan Option="2" ring="fr6210" MT="200" DT="210" MN="0" DN="0"/>
    <plan Option="3" ring="sk6" MT="350" DT="150" MN="350" DN="150"/>
</item>
</nomogram>
<nomogram name="largenipple">
<item ESF="-1/3" CYL="-5/5">
    <plan Option="1" ring="in7" MT="300" DT="150" MN="300" DN="150"/>
    <plan Option="2" ring="fr6210" MT="150" DT="210" MN="0" DN="0"/>
    <plan Option="3" ring="kr5355" MT="150" DT="355" MN="0" DN="0"/>
</item>
<item ESF="-2" CYL="-5/5">
    <plan Option="1" ring="in7" MT="350" DT="150" MN="350" DN="150"/>
    <plan Option="2" ring="fr6210" MT="150" DT="210" MN="0" DN="0"/>
    <plan Option="3" ring="kr5355" MT="150" DT="355" MN="0" DN="0"/>
</item>
<item ESF="-3" CYL="-5/5">
    <plan Option="1" ring="fr6210" MT="150" DT="210" MN="0" DN="0"/>
    <plan Option="2" ring="in7" MT="400" DT="150" MN="400" DN="150"/>
```

```xml
    <plan Option="3" ring="kr5355" MT="200" DT="355" MN="0" DN="0"/>
</item>
<item ESF="-4" CYL="-5/5">
    <plan Option="1" ring="fr6210" MT="200" DT="210" MN="0" DN="0"/>
    <plan Option="2" ring="sk6" MT="350" DT="150" MN="350" DN="150"/>
    <plan Option="3" ring="kr5355" MT="200" DT="355" MN="0" DN="0"/>
</item>
<item ESF="-8/-5" CYL="-5/5">
    <plan Option="1" ring="kr5355" MT="200" DT="355" MN="0" DN="0"/>
    <plan Option="2" ring="fr6210" MT="200" DT="210" MN="0" DN="0"/>
    <plan Option="3" ring="sk6" MT="350" DT="150" MN="350" DN="150"/>
</item>
</nomogram>
<nomogram name="duck">
<item ESF="0/1" CYL="-2/2">
    <plan Option="1" ring="sk6" MT="300" DT="150" MN="0" DN="0"/>
    <plan Option="2" ring="fr6" MT="150" DT="120" MN="0" DN="0"/>
</item>
<item ESF="-1/1" CYL="-3">
    <plan Option="1" ring="frsk6" MT="150" DT="140" MN="300" DN="130"/>
    <plan Option="2" ring="fr6" MT="150" DT="140" MN="0" DN="0"/>
</item>
<item ESF="-1/1" CYL="-4">
    <plan Option="1" ring="frsk6" MT="150" DT="140" MN="300" DN="130"/>
    <plan Option="2" ring="fr6" MT="150" DT="140" MN="0" DN="0"/>
</item>
<item ESF="-1/1" CYL="-5">
    <plan Option="1" ring="frsk6" MT="200" DT="140" MN="350" DN="130"/>
    <plan Option="2" ring="fr6" MT="150" DT="140" MN="150" DN="90"/>
</item>
<item ESF="-1/1" CYL="-6">
    <plan Option="1" ring="frsk6" MT="200" DT="140" MN="350" DN="130"/>
    <plan Option="2" ring="fr6" MT="150" DT="140" MN="150" DN="120"/>
    <plan Option="3" ring="fr5" MT="150" DT="160" MN="150" DN="120"/>
</item>
<item ESF="-1/1" CYL="-7">
    <plan Option="1" ring="fr6" MT="200" DT="140" MN="150" DN="120"/>
    <plan Option="2" ring="fr6" MT="150" DT="140" MN="150" DN="120"/>
    <plan Option="3" ring="fr5" MT="200" DT="160" MN="150" DN="120"/>
</item>
<item ESF="-1/1" CYL="-8">
    <plan Option="1" ring="fr6" MT="200" DT="140" MN="150" DN="120"/>
    <plan Option="2" ring="fr6" MT="150" DT="140" MN="150" DN="120"/>
    <plan Option="3" ring="fr5" MT="200" DT="160" MN="150" DN="120"/>
</item>
<item ESF="-1/1" CYL="-9">
    <plan Option="1" ring="fr5" MT="150" DT="160" MN="150" DN="120"/>
</item>
<item ESF="-2/-1" CYL="0/2">
    <plan Option="1" ring="sk6" MT="300" DT="150" MN="0" DN="0"/>
    <plan Option="2" ring="fr6" MT="150" DT="120" MN="0" DN="0"/>
</item>
<item ESF="-3" CYL="-0/2">
    <plan Option="1" ring="sk6" MT="300" DT="150" MN="300" DN="150"/>
    <plan Option="2" ring="fr6" MT="150" DT="120" MN="0" DN="0"/>
</item>
<item ESF="-4" CYL="-0/2">
    <plan Option="1" ring="sk6" MT="350" DT="150" MN="350" DN="150"/>
    <plan Option="2" ring="frsk6" MT="150" DT="140" MN="300" DN="150"/>
</item>
<item ESF="-5" CYL="-0/2">
    <plan Option="1" ring="sk6" MT="400" DT="150" MN="400" DN="150"/>
    <plan Option="2" ring="frsk6" MT="150" DT="140" MN="300" DN="150"/>
</item>
<item ESF="-6" CYL="-0/2">
    <plan Option="1" ring="sk6" MT="400" DT="150" MN="400" DN="150"/>
    <plan Option="2" ring="frsk6" MT="150" DT="140" MN="350" DN="150"/>
</item>
<item ESF="-8/-7" CYL="-0/2">
    <plan Option="1" ring="sk6" MT="450" DT="150" MN="450" DN="150"/>
    <plan Option="2" ring="frsk6" MT="150" DT="140" MN="350" DN="150"/>
</item>
<item ESF="-8/-7" CYL="-0/2">
    <plan Option="1" ring="sk6" MT="450" DT="150" MN="450" DN="150"/>
    <plan Option="2" ring="frsk6" MT="150" DT="140" MN="350" DN="150"/>
</item>
<item ESF="-1" CYL="-1">
    <plan Option="1" ring="sk6" MT="300" DT="150" MN="300" DN="150"/>
    <plan Option="2" ring="fr6" MT="150" DT="120" MN="0" DN="0"/>
</item>
<item ESF="-1" CYL="-2">
    <plan Option="1" ring="fr6" MT="150" DT="120" MN="0" DN="0"/>
    <plan Option="2" ring="frsk6" MT="150" DT="120" MN="300" DN="150"/>
</item>
<item ESF="-3/-2" CYL="-1">
    <plan Option="1" ring="sk6" MT="300" DT="150" MN="300" DN="150"/>
    <plan Option="2" ring="frsk6" MT="150" DT="120" MN="300" DN="150"/>
```

```xml
</item>
<item ESF="-3/-2" CYL="-2">
  <plan Option="1" ring="sk6" MT="300" DT="150" MN="250" DN="130"/>
  <plan Option="2" ring="frsk6" MT="150" DT="120" MN="300" DN="150"/>
</item>
<item ESF="-4/-2" CYL="-4">
  <plan Option="1" ring="frsk6" MT="200" DT="140" MN="300" DN="130"/>
  <plan Option="2" ring="frsk6" MT="150" DT="140" MN="300" DN="130"/>
</item>
<item ESF="-6/-3" CYL="-5">
  <plan Option="1" ring="frsk6" MT="200" DT="140" MN="350" DN="130"/>
  <plan Option="2" ring="frsk6" MT="200" DT="140" MN="300" DN="150"/>
</item>
<item ESF="-6/-3" CYL="-6">
  <plan Option="1" ring="fr6" MT="150" DT="140" MN="150" DN="120"/>
  <plan Option="2" ring="frsk6" MT="150" DT="140" MN="350" DN="130"/>
  <plan Option="3" ring="fr5" MT="150" DT="160" MN="150" DN="120"/>
</item>
<item ESF="-6/-2" CYL="-7">
  <plan Option="1" ring="fr6" MT="200" DT="140" MN="150" DN="120"/>
  <plan Option="2" ring="frsk6" MT="200" DT="140" MN="350" DN="130"/>
  <plan Option="3" ring="fr5" MT="150" DT="160" MN="150" DN="120"/>
</item>
<item ESF="-6/-2" CYL="-8">
  <plan Option="1" ring="fr6" MT="200" DT="140" MN="150" DN="120"/>
  <plan Option="2" ring="frsk6" MT="200" DT="140" MN="350" DN="130"/>
  <plan Option="3" ring="fr5" MT="200" DT="160" MN="150" DN="120"/>
</item>
<item ESF="-6/-2" CYL="-9">
  <plan Option="1" ring="fr5" MT="200" DT="160" MN="150" DN="120"/>
</item>
<item ESF="-7" CYL="-8/-7">
  <plan Option="1" ring="fr6" MT="200" DT="140" MN="150" DN="120"/>
  <plan Option="2" ring="frsk6" MT="200" DT="140" MN="400" DN="130"/>
  <plan Option="3" ring="fr5" MT="200" DT="160" MN="150" DN="140"/>
</item>
<item ESF="-8" CYL="-8/-7">
  <plan Option="1" ring="fr6" MT="200" DT="140" MN="150" DN="120"/>
  <plan Option="2" ring="frsk6" MT="200" DT="140" MN="450" DN="130"/>
  <plan Option="3" ring="fr5" MT="200" DT="160" MN="150" DN="140"/>
</item>
<item ESF="-8/-7" CYL="-9">
  <plan Option="1" ring="fr5" MT="200" DT="160" MN="150" DN="140"/>
</item>
<item ESF="-7" CYL="-6">
  <plan Option="1" ring="fr6" MT="150" DT="140" MN="150" DN="120"/>
  <plan Option="2" ring="frsk6" MT="150" DT="140" MN="400" DN="130"/>
  <plan Option="3" ring="fr5" MT="150" DT="160" MN="150" DN="140"/>
</item>
<item ESF="-8" CYL="-6">
  <plan Option="1" ring="fr6" MT="150" DT="140" MN="150" DN="120"/>
  <plan Option="2" ring="frsk6" MT="150" DT="140" MN="450" DN="130"/>
  <plan Option="3" ring="fr5" MT="150" DT="160" MN="150" DN="140"/>
</item>
<item ESF="-7" CYL="-5">
  <plan Option="1" ring="frsk6" MT="200" DT="140" MN="350" DN="130"/>
  <plan Option="2" ring="frsk6" MT="200" DT="140" MN="400" DN="150"/>
</item>
<item ESF="-8" CYL="-5">
  <plan Option="1" ring="frsk6" MT="200" DT="140" MN="350" DN="130"/>
  <plan Option="2" ring="frsk6" MT="200" DT="140" MN="450" DN="150"/>
</item>
<item ESF="-2" CYL="-3">
  <plan Option="1" ring="frsk6" MT="150" DT="140" MN="300" DN="130"/>
  <plan Option="2" ring="fr6" MT="150" DT="140" MN="0" DN="0"/>
</item>
<item ESF="-2" CYL="-5">
  <plan Option="1" ring="frsk6" MT="200" DT="140" MN="350" DN="130"/>
  <plan Option="2" ring="frsk6" MT="150" DT="140" MN="350" DN="130"/>
</item>
<item ESF="-2" CYL="-6">
  <plan Option="1" ring="frsk6" MT="200" DT="140" MN="350" DN="130"/>
  <plan Option="2" ring="frsk6" MT="150" DT="140" MN="450" DN="130"/>
  <plan Option="3" ring="fr5" MT="150" DT="160" MN="150" DN="120"/>
</item>
<item ESF="-3" CYL="-3">
  <plan Option="1" ring="frsk6" MT="150" DT="140" MN="300" DN="130"/>
  <plan Option="2" ring="frsk6" MT="150" DT="140" MN="350" DN="130"/>
</item>
<item ESF="-4" CYL="-2/-1">
  <plan Option="1" ring="sk6" MT="350" DT="150" MN="350" DN="150"/>
  <plan Option="2" ring="frsk6" MT="150" DT="120" MN="350" DN="150"/>
</item>
<item ESF="-4" CYL="-3">
  <plan Option="1" ring="frsk6" MT="150" DT="140" MN="300" DN="130"/>
  <plan Option="2" ring="frsk6" MT="150" DT="140" MN="350" DN="150"/>
```

```xml
<item ESF="-5" CYL="-1">
  <plan Option="1" ring="sk6" MT="400" DT="150" MN="400" DN="150"/>
  <plan Option="2" ring="frsk6" MT="150" DT="120" MN="350" DN="150"/>
</item>
<item ESF="-8/-6" CYL="-1">
  <plan Option="1" ring="sk6" MT="400" DT="150" MN="400" DN="150"/>
  <plan Option="2" ring="frsk6" MT="150" DT="120" MN="350" DN="150"/>
</item>
<item ESF="-5" CYL="-2">
  <plan Option="1" ring="sk6" MT="350" DT="150" MN="400" DN="130"/>
  <plan Option="2" ring="frsk6" MT="150" DT="120" MN="350" DN="150"/>
</item>
<item ESF="-5" CYL="-3">
  <plan Option="1" ring="frsk6" MT="150" DT="140" MN="350" DN="130"/>
  <plan Option="2" ring="frsk6" MT="150" DT="120" MN="350" DN="150"/>
</item>
<item ESF="-5" CYL="-4">
  <plan Option="1" ring="frsk6" MT="200" DT="140" MN="350" DN="130"/>
  <plan Option="2" ring="frsk6" MT="150" DT="140" MN="350" DN="150"/>
</item>
<item ESF="-7/-6" CYL="-2">
  <plan Option="1" ring="sk6" MT="400" DT="130" MN="450" DN="130"/>
  <plan Option="2" ring="frsk6" MT="150" DT="120" MN="450" DN="150"/>
</item>
<item ESF="-8" CYL="-2">
  <plan Option="1" ring="frsk6" MT="150" DT="140" MN="350" DN="130"/>
  <plan Option="2" ring="frsk6" MT="150" DT="120" MN="400" DN="150"/>
</item>
<item ESF="-8/-6" CYL="-3">
  <plan Option="1" ring="frsk6" MT="150" DT="140" MN="400" DN="130"/>
  <plan Option="2" ring="frsk6" MT="150" DT="140" MN="350" DN="130"/>
</item>
<item ESF="-8/-6" CYL="-4">
  <plan Option="1" ring="frsk6" MT="150" DT="140" MN="400" DN="130"/>
  <plan Option="2" ring="frsk6" MT="150" DT="140" MN="400" DN="150"/>
</item>
</nomogram>
<nomogram name="crossaint">
<item ESF="0/1" CYL="-2/2">
  <plan Option="1" ring="sk6" MT="300" DT="150" MN="0" DN="0"/>
  <plan Option="2" ring="fr6" MT="150" DT="120" MN="0" DN="0"/>
</item>
<item ESF="-1/1" CYL="-3">
  <plan Option="1" ring="frsk6" MT="150" DT="140" MN="300" DN="140"/>
  <plan Option="2" ring="fr6" MT="150" DT="140" MN="0" DN="0"/>
</item>
<item ESF="-1/1" CYL="-4">
  <plan Option="1" ring="frsk6" MT="150" DT="140" MN="300" DN="130"/>
  <plan Option="2" ring="fr6" MT="150" DT="140" MN="0" DN="0"/>
</item>
<item ESF="-1/1" CYL="-5">
  <plan Option="1" ring="frsk6" MT="200" DT="140" MN="350" DN="130"/>
  <plan Option="2" ring="fr6" MT="150" DT="140" MN="150" DN="90"/>
</item>
<item ESF="-1/1" CYL="-6">
  <plan Option="1" ring="frsk6" MT="200" DT="140" MN="350" DN="130"/>
  <plan Option="2" ring="fr6" MT="150" DT="140" MN="150" DN="120"/>
  <plan Option="3" ring="fr5" MT="150" DT="160" MN="150" DN="120"/>
</item>
<item ESF="-1/1" CYL="-7">
  <plan Option="1" ring="fr6" MT="200" DT="140" MN="150" DN="120"/>
  <plan Option="2" ring="fr6" MT="150" DT="140" MN="150" DN="120"/>
  <plan Option="3" ring="fr5" MT="200" DT="160" MN="150" DN="120"/>
</item>
<item ESF="-1/1" CYL="-8">
  <plan Option="1" ring="fr6" MT="200" DT="140" MN="150" DN="120"/>
  <plan Option="2" ring="fr6" MT="150" DT="140" MN="150" DN="120"/>
  <plan Option="3" ring="fr5" MT="200" DT="160" MN="150" DN="120"/>
</item>
<item ESF="-1/1" CYL="-9/">
  <plan Option="1" ring="fr5" MT="150" DT="160" MN="150" DN="120"/>
</item>
<item ESF="-2/-1" CYL="0/2">
  <plan Option="1" ring="sk6" MT="300" DT="150" MN="0" DN="0"/>
  <plan Option="2" ring="fr6" MT="150" DT="120" MN="0" DN="0"/>
</item>
<item ESF="-3" CYL="-0/2">
  <plan Option="1" ring="sk6" MT="300" DT="150" MN="300" DN="150"/>
  <plan Option="2" ring="fr6" MT="150" DT="120" MN="0" DN="0"/>
</item>
<item ESF="-4" CYL="-0/2">
  <plan Option="1" ring="sk6" MT="350" DT="150" MN="350" DN="150"/>
  <plan Option="2" ring="frsk6" MT="150" DT="140" MN="300" DN="150"/>
</item>
<item ESF="-5" CYL="-0/2">
  <plan Option="1" ring="sk6" MT="400" DT="150" MN="400" DN="150"/>
  <plan Option="2" ring="frsk6" MT="150" DT="140" MN="300" DN="150"/>
```

</item>
<item ESF="-6" CYL="-0/2">
  <plan Option="1" ring="sk6" MT="400" DT="150" MN="400" DN="150"/>
  <plan Option="2" ring="frsk6" MT="150" DT="140" MN="350" DN="150"/>
</item>
<item ESF="-8/-7" CYL="-0/2">
  <plan Option="1" ring="sk6" MT="450" DT="150" MN="450" DN="150"/>
  <plan Option="2" ring="frsk6" MT="150" DT="140" MN="350" DN="150"/>
</item>
<item ESF="-8/-7" CYL="-0/2">
  <plan Option="1" ring="sk6" MT="450" DT="150" MN="450" DN="150"/>
  <plan Option="2" ring="frsk6" MT="150" DT="140" MN="350" DN="150"/>
</item>
<item ESF="-1" CYL="-1">
  <plan Option="1" ring="sk6" MT="300" DT="150" MN="300" DN="150"/>
  <plan Option="2" ring="fr6" MT="150" DT="120" MN="0" DN="0"/>
</item>
<item ESF="-1" CYL="-2">
  <plan Option="1" ring="fr6" MT="150" DT="120" MN="0" DN="0"/>
  <plan Option="2" ring="frsk6" MT="150" DT="120" MN="300" DN="150"/>
</item>
<item ESF="-3/-2" CYL="-1">
  <plan Option="1" ring="sk6" MT="300" DT="150" MN="300" DN="150"/>
  <plan Option="2" ring="frsk6" MT="150" DT="120" MN="300" DN="150"/>
</item>
<item ESF="-3/-2" CYL="-2">
  <plan Option="1" ring="sk6" MT="300" DT="150" MN="250" DN="130"/>
  <plan Option="2" ring="frsk6" MT="150" DT="120" MN="300" DN="150"/>
</item>
<item ESF="-4/-2" CYL="-4">
  <plan Option="1" ring="frsk6" MT="200" DT="140" MN="300" DN="130"/>
  <plan Option="2" ring="frsk6" MT="150" DT="120" MN="300" DN="130"/>
</item>
<item ESF="-6/-3" CYL="-5">
  <plan Option="1" ring="frsk6" MT="200" DT="140" MN="350" DN="130"/>
  <plan Option="2" ring="frsk6" MT="200" DT="140" MN="300" DN="150"/>
</item>
<item ESF="-6/-3" CYL="-6">
  <plan Option="1" ring="fr6" MT="150" DT="140" MN="150" DN="120"/>
  <plan Option="2" ring="frsk6" MT="150" DT="140" MN="350" DN="130"/>
  <plan Option="3" ring="fr5" MT="150" DT="160" MN="150" DN="120"/>
</item>
<item ESF="-6/-2" CYL="-7">
  <plan Option="1" ring="fr6" MT="200" DT="140" MN="150" DN="120"/>
  <plan Option="2" ring="frsk6" MT="200" DT="140" MN="350" DN="130"/>
  <plan Option="3" ring="fr5" MT="150" DT="160" MN="150" DN="120"/>
</item>
<item ESF="-6/-2" CYL="-8">
  <plan Option="1" ring="fr6" MT="200" DT="140" MN="150" DN="120"/>
  <plan Option="2" ring="frsk6" MT="200" DT="140" MN="350" DN="130"/>
  <plan Option="3" ring="fr5" MT="200" DT="160" MN="150" DN="120"/>
</item>
<item ESF="-6/-2" CYL="-9">
  <plan Option="1" ring="fr5" MT="200" DT="160" MN="150" DN="120"/>
</item>
<item ESF="-7" CYL="-8/-7">
  <plan Option="1" ring="fr6" MT="200" DT="140" MN="150" DN="120"/>
  <plan Option="2" ring="frsk6" MT="200" DT="140" MN="400" DN="130"/>
  <plan Option="3" ring="fr5" MT="200" DT="160" MN="150" DN="140"/>
</item>
<item ESF="-8" CYL="-8/-7">
  <plan Option="1" ring="fr6" MT="200" DT="140" MN="150" DN="120"/>
  <plan Option="2" ring="frsk6" MT="200" DT="140" MN="450" DN="130"/>
  <plan Option="3" ring="fr5" MT="200" DT="160" MN="150" DN="140"/>
</item>
<item ESF="-8/-7" CYL="-9">
  <plan Option="1" ring="fr5" MT="200" DT="160" MN="150" DN="140"/>
</item>
<item ESF="-7" CYL="-6">
  <plan Option="1" ring="fr6" MT="150" DT="140" MN="150" DN="120"/>
  <plan Option="2" ring="frsk6" MT="150" DT="140" MN="400" DN="130"/>
  <plan Option="3" ring="fr5" MT="150" DT="160" MN="150" DN="140"/>
</item>
<item ESF="-8" CYL="-6">
  <plan Option="1" ring="fr6" MT="150" DT="140" MN="150" DN="120"/>
  <plan Option="2" ring="frsk6" MT="150" DT="140" MN="450" DN="130"/>
  <plan Option="3" ring="fr5" MT="150" DT="160" MN="150" DN="140"/>
</item>
<item ESF="-7" CYL="-5">
  <plan Option="1" ring="frsk6" MT="200" DT="140" MN="350" DN="130"/>
  <plan Option="2" ring="frsk6" MT="200" DT="140" MN="400" DN="150"/>
</item>
<item ESF="-8" CYL="-5">
  <plan Option="1" ring="frsk6" MT="200" DT="140" MN="350" DN="130"/>
  <plan Option="2" ring="frsk6" MT="200" DT="140" MN="450" DN="150"/>
</item>
<item ESF="-2" CYL="-3">
  <plan Option="1" ring="frsk6" MT="150" DT="140" MN="300" DN="130"/>
  <plan Option="2" ring="fr6" MT="150" DT="140" MN="0" DN="0"/>

```
</item>
<item ESF="-2" CYL="-5">
  <plan Option="1" ring="frsk6" MT="200" DT="140" MN="350" DN="130"/>
  <plan Option="2" ring="frsk6" MT="140" DT="150" MN="350" DN="130"/>
</item>
<item ESF="-2" CYL="-6">
  <plan Option="1" ring="frsk6" MT="200" DT="140" MN="350" DN="130"/>
  <plan Option="2" ring="frsk6" MT="150" DT="140" MN="450" DN="130"/>
  <plan Option="3" ring="fr5" MT="150" DT="160" MN="150" DN="120"/>
</item>
<item ESF="-3" CYL="-3">
  <plan Option="1" ring="frsk6" MT="150" DT="140" MN="300" DN="130"/>
  <plan Option="2" ring="frsk6" MT="150" DT="140" MN="350" DN="130"/>
</item>
<item ESF="-4" CYL="-2/-1">
  <plan Option="1" ring="sk6" MT="350" DT="150" MN="350" DN="150"/>
  <plan Option="2" ring="frsk6" MT="150" DT="120" MN="350" DN="150"/>
</item>
<item ESF="-4" CYL="-3">
  <plan Option="1" ring="frsk6" MT="150" DT="140" MN="300" DN="130"/>
  <plan Option="2" ring="frsk6" MT="150" DT="140" MN="350" DN="150"/>
</item>
<item ESF="-5" CYL="-1">
  <plan Option="1" ring="sk6" MT="400" DT="150" MN="400" DN="150"/>
  <plan Option="2" ring="frsk6" MT="150" DT="120" MN="350" DN="150"/>
</item>
<item ESF="-8/-6" CYL="-1">
  <plan Option="1" ring="sk6" MT="400" DT="150" MN="400" DN="150"/>
  <plan Option="2" ring="frsk6" MT="150" DT="120" MN="350" DN="150"/>
</item>
<item ESF="-5" CYL="-2">
  <plan Option="1" ring="sk6" MT="350" DT="150" MN="400" DN="130"/>
  <plan Option="2" ring="frsk6" MT="150" DT="120" MN="350" DN="150"/>
</item>
<item ESF="-5" CYL="-3">
  <plan Option="1" ring="frsk6" MT="150" DT="140" MN="350" DN="130"/>
  <plan Option="2" ring="frsk6" MT="150" DT="120" MN="350" DN="150"/>
</item>
<item ESF="-5" CYL="-4">
  <plan Option="1" ring="frsk6" MT="200" DT="140" MN="350" DN="130"/>
  <plan Option="2" ring="frsk6" MT="150" DT="140" MN="350" DN="150"/>
</item>
<item ESF="-7/-6" CYL="-2">
  <plan Option="1" ring="sk6" MT="400" DT="130" MN="450" DN="130"/>
  <plan Option="2" ring="frsk6" MT="150" DT="120" MN="450" DN="150"/>
</item>
<item ESF="-8" CYL="-2">
  <plan Option="1" ring="frsk6" MT="150" DT="140" MN="350" DN="130"/>
  <plan Option="2" ring="frsk6" MT="150" DT="120" MN="400" DN="150"/>
</item>
<item ESF="-8/-6" CYL="-3">
  <plan Option="1" ring="frsk6" MT="150" DT="140" MN="400" DN="130"/>
  <plan Option="2" ring="frsk6" MT="150" DT="140" MN="350" DN="130"/>
</item>
<item ESF="-8/-6" CYL="-4">
  <plan Option="1" ring="frsk6" MT="150" DT="140" MN="400" DN="130"/>
  <plan Option="2" ring="frsk6" MT="150" DT="140" MN="400" DN="150"/>
</item>
</nomogram>
<nomogram name="pelluciddegeneration">
<item ESF="0/5" CYL="-1/5">
  <plan Option="1" ring="frsk6" MT="150" DT="120" MN="250" DN="130"/>
  <plan Option="2" ring="fr6" MT="150" DT="140" MN="0" DN="0"/>
  <plan Option="3" ring="sk6" MT="250" DT="130" MN="250" DN="130"/>
</item>
<item ESF="0/5" CYL="-2">
  <plan Option="1" ring="fr6" MT="150" DT="120" MN="0" DN="0"/>
  <plan Option="2" ring="frsk6" MT="150" DT="120" MN="250" DN="130"/>
  <plan Option="3" ring="sk6" MT="250" DT="150" MN="250" DN="130"/>
</item>
<item ESF="-11/5.01" CYL="-3/0">
  <plan Option="1" ring="frsk6" MT="150" DT="140" MN="300" DN="150"/>
  <plan Option="2" ring="fr6" MT="150" DT="140" MN="250" DN="150"/>
  <plan Option="3" ring="sk6" MT="300" DT="150" MN="250" DN="130"/>
</item>
<item ESF="-11/5" CYL="-4">
  <plan Option="1" ring="frsk6" MT="150" DT="140" MN="300" DN="130"/>
  <plan Option="2" ring="fr6" MT="150" DT="140" MN="150" DN="120"/>
  <plan Option="3" ring="sk6" MT="350" DT="130" MN="300" DN="130"/>
</item>
<item ESF="-11/5" CYL="-5">
  <plan Option="1" ring="fr6" MT="150" DT="140" MN="150" DN="120"/>
  <plan Option="2" ring="frsk6" MT="150" DT="140" MN="300" DN="130"/>
  <plan Option="3" ring="fr5" MT="150" DT="160" MN="150" DN="120"/>
</item>
<item ESF="-11/5" CYL="-6">
  <plan Option="1" ring="fr6" MT="200" DT="140" MN="150" DN="120"/>
  <plan Option="2" ring="frsk6" MT="200" DT="140" MN="350" DN="130"/>
```

```
<plan Option="3" ring="fr5" MT="150" DT="160"
MN="150" DN="120"/>
</item>
<item ESF="-11/5" CYL="-7">
    <plan Option="1" ring="fr6" MT="200" DT="140"
MN="200" DN="120"/>
    <plan Option="2" ring="fr5" MT="200" DT="160"
MN="150" DN="160"/>
</item>
<item ESF="-11/5" CYL="-8">
    <plan Option="1" ring="fr5" MT="200" DT="160"
MN="150" DN="160"/>
    <plan Option="2" ring="fr6" MT="200" DT="140"
MN="200" DN="90"/>
</item>
<item ESF="-11/5" CYL="-11/-9">
    <plan Option="1" ring="fr5" MT="250" DT="160"
MN="200" DN="120"/>
    <plan Option="2" ring="fr6" MT="200" DT="140"
MN="200" DN="120"/>
</item>
</nomogram>
```

What is claimed is:

1. A method of treating keratoconus in an eye of a patient, the method comprising:
   measuring a surface of a cornea of the eye to acquire eye topography data;
   based on the eye topography data, selecting a topographic pattern from a plurality of topographic patterns displayed in a graphical user interface;
   entering a plurality of vision corrective parameters for the eye of the patient into the graphical user interface;
   actuating a processing module associated with the graphical user interface to obtain a surgical plan based on the selected topographic pattern and the plurality of entered vision corrective parameters;
   reviewing intrastromal corneal ring segment (ICRS) implantation surgery parameters specified by the surgical plan and displayed in the graphical user interface, wherein the ICRS implantation surgery parameters include specification of at least one ICRS; and
   performing implantation surgery of the at least one ICRS into the eye of the patient according to the surgical plan.

2. The method of claim 1 wherein:
   the ICRS implantation surgery parameters include an incision axis; and
   the performing implantation surgery includes making an incision in the eye of the patient at the incision axis.

3. The method of claim 1 wherein:
   the selecting the topographic pattern further comprises selecting a topographic sub-pattern of the selected topographic pattern from a plurality of topographic sub-patterns displayed in the graphical user interface; and
   the surgical plan is based on the selected topographic sub-pattern.

4. The method of claim 1 wherein the plurality of vision corrective parameters includes at least two of a sphere power, a cylinder power, a pachymetry, a cylinder axis and a best spectacle-corrected visual acuity.

5. The method of claim 1 wherein the specification of the at least one ICRS includes specification of a nasal ICRS and a temporal ICRS, and wherein each of the nasal ICRS and the temporal ICRS is specified by an ICRS family, a thickness, and an arc length.

6. The method of claim 1 wherein:
   the graphical user interface displays a plurality of surgical plans; and
   the method includes selecting one of the plurality of surgical plans as the surgical plan.

7. A computer-assisted method of treating keratoconus in an eye of a patient, the method comprising:
   measuring a surface of a cornea of the eye to acquire eye topography data;
   presenting, by a computer system, a graphical display of a plurality of topographic patterns;
   based on the eye topography data, selecting a topographic pattern from the plurality of topographic patterns;
   presenting, by the computer system, an interface that provides for entry of a plurality of vision corrective parameters for the eye of the patient;
   entering the plurality of vision corrective parameters to the computer system;
   by the computer system, obtaining a surgical plan from a data store based on the selected topographic pattern and the plurality of entered vision corrective parameters;
   displaying intrastromal corneal ring segment (ICRS) implantation surgery parameters specified by the surgical plan, wherein the ICRS implantation surgery parameters include specification of at least one ICRS;
   obtaining the at least one ICRS; and
   performing implantation surgery of the at least one ICRS into the eye of the patient according to the surgical plan.

8. The computer-assisted method of claim 7 further comprising:
   in response to the topographic pattern corresponding to a plurality of topographic sub-patterns, presenting, by the computer system, a graphical display of the plurality of topographic sub-patterns; and
   based on the eye topography data, selecting a topographic subpattern from the plurality of topographic sub-patterns,
   wherein the computer system obtains the surgical plan based on the selected topographic sub-pattern and the plurality of entered vision corrective parameters.

9. The computer-assisted method of claim 7 wherein the specification of the at least one ICRS includes specification of a nasal ICRS and a temporal ICRS, and
   wherein each of the nasal ICRS and the temporal ICRS is specified by an ICRS family, a thickness, and an arc length.

10. The computer-assisted method of claim 7 further comprising, in response to recognition that the data store includes a plurality of surgical plans based on the selected topographic pattern and the plurality of entered vision corrective parameters:
    displaying, by the computer system, an indication that the plurality of surgical plans is available; and
    selecting one of the plurality of surgical plans as the surgical plan.

11. The computer-assisted method of claim 7 wherein the plurality of vision corrective parameters includes at least two of a sphere power, a cylinder power, a pachymetry, a cylinder axis and a best spectacle-corrected visual acuity.

12. The computer-assisted method of claim 11 wherein:
    the plurality of vision corrective parameters includes the sphere power and the cylinder power;
    the method further comprises:
       by the computer system, generating a second sphere power by selectively adjusting the sphere power; and
       by the computer system, generating a second cylinder power by selectively adjusting the cylinder power; and wherein the computer system obtains the surgical plan based on the selected topographic pattern, the second sphere power, and the second cylinder power.

13. The computer-assisted method of claim 12 wherein: the plurality of vision corrective parameters includes the sphere power, the cylinder power, and the pachymetry;
the generating the second sphere power includes:
in response to the pachymetry being less than 430, decrementing an absolute value of the sphere power to arrive at the second sphere power;
in response to the pachymetry being greater than 550, incrementing an absolute value of the sphere power to arrive at the second sphere power; and
in response to the pachymetry being between 430 and 550, setting the second sphere power equal to the sphere power; and the generating the second cylinder power includes:
in response to the pachymetry being less than 430, decrementing an absolute value of the cylinder power to arrive at the second cylinder power;
in response to the pachymetry being greater than 550, incrementing an absolute value of the cylinder power to arrive at the second cylinder power; and
in response to the pachymetry being between 430 and 550, setting the second cylinder power equal to the cylinder power.

14. The computer-assisted method of claim 7 wherein: the method includes determining, by the computer system, an incision axis based on the plurality of entered vision corrective parameters;
the ICRS implantation surgery parameters include the incision axis; and
the performing implantation surgery includes making an incision in the eye of the patient at the incision axis.

15. The computer-assisted method of claim 14 wherein: the plurality of entered vision corrective parameters includes a cylinder axis; and
the determining the incision axis includes
in response to the cylinder axis being between 0 degrees and 90 degrees, setting the incision axis to be equal to the cylinder axis plus 90 degrees; and
in response to the cylinder axis being between 90 degrees and 180 degrees, setting the incision axis to be equal to the cylinder axis minus 90 degrees.

16. The computer-assisted method of claim 7 further comprising ordering, by the computer system, the at least one ICRS.

17. An apparatus for treating keratoconus in an eye of a patient, the apparatus comprising:
a processor that executes code to implement a user interface module, wherein the user interface module is configured to present:
a graphical display of a plurality of topographic patterns corresponding to different potential measured corneal topographies of the eye of the patient, and
an interface that provides for entry of a plurality of vision corrective parameters for the eye of the patient;
a data input module configured to receive the plurality of entered vision corrective parameters and a selection of one of the plurality of topographic patterns;
a patient data store configured to store the plurality of entered vision corrective parameters and the selected topographic pattern;
a nomogram data store configured to store a plurality of nomograms, wherein each nomogram specifies intrastromal corneal ring segment (ICRS) implantation surgery parameters, and wherein the ICRS implantation surgery parameters include specification of at least one ICRS;
a surgical plan determination module configured to identify a nomogram from the nomogram data store based on the selected topographic pattern and the plurality of entered vision corrective parameters; and
a presentation module configured to display the ICRS implantation surgery parameters specified by the identified nomogram.

18. The apparatus of claim 17 further comprising an ordering module configured to place an order for the at least one ICRS.

19. The apparatus of claim 17 wherein:
the user interface module is further configured to, in response to the selected topographic pattern corresponding to a plurality of topographic sub-patterns, present a graphical display of the plurality of topographic sub-patterns;
the data input module is configured to receive a selection of one of the plurality of topographic sub-patterns; and
the surgical plan determination module is configured to select the identified nomogram from the nomogram data store based on the selected topographic sub-pattern and the plurality of entered vision corrective parameters.

20. The apparatus of claim 17 wherein the specification of the at least one ICRS includes specification of a nasal ICRS and a temporal ICRS, and wherein each of the nasal ICRS and the temporal ICRS is specified by an ICRS family, a thickness, and an arc length.

21. The apparatus of claim 17 further comprising: a surgical plan selection module configured to, in response to the
selected topographic pattern and the plurality of entered vision corrective parameters corresponding to a first set of nomograms in the nomogram data store, receive selection of one of the first set of nomograms as the identified nomogram,
wherein the presentation module is configured to display the ICRS implantation surgery parameters specified by the identified nomogram.

22. The apparatus of claim 17 wherein:
the plurality of entered vision corrective parameters includes a sphere power, a cylinder power, and a pachymetry;
the apparatus further comprises a parameter calculation module configured to:
generate a second sphere power by selectively adjusting the sphere power; and
generate a second cylinder power by selectively adjusting the cylinder power; and
the surgical plan determination module is configured to identify the identified nomogram from the nomogram data store based on the selected topographic pattern, the second sphere power, and the second cylinder power.

23. The apparatus of claim 22 wherein:
the parameter calculation module is configured to generate the second sphere power by:
in response to the pachymetry being less than 430, decrementing an absolute value of the sphere power to arrive at the second sphere power;
in response to the pachymetry being greater than 550, incrementing an absolute value of the sphere power to arrive at the second sphere power in response to the pachymetry being greater than 550; and in response to the pachymetry being between 430 and 550, setting the second sphere power equal to the sphere power; and the parameter calculation module is configured to generate the second cylinder power by:

in response to the pachymetry being less than 430, decrementing an absolute value of the cylinder power to arrive at the second cylinder power;

in response to the pachymetry being greater than 550, incrementing an absolute value of the cylinder power to arrive at the second cylinder power; and in response to the pachymetry being between 430 and 550, setting the second cylinder power equal to the cylinder power.

24. The apparatus of claim 17 further comprising a parameter calculation module configured to determine an incision axis based on the plurality of entered vision corrective parameters, wherein the ICRS implantation surgery parameters include the incision axis.

25. The apparatus of claim 24 wherein:

the plurality of entered vision corrective parameters includes a cylinder axis; and the parameter calculation module is configured to determine the incision axis by:

in response to the cylinder axis being between 0 degrees and 90 degrees, setting the incision axis to be equal to the cylinder axis plus 90 degrees; and in response to the cylinder axis being between 90 degrees and 180 degrees, setting the incision axis to be equal to the cylinder axis minus 90 degrees.

26. The apparatus of claim 17 further comprising a network communication module, wherein the nomogram data store is configured to receive updated nomograms via the network communication module.

27. A non-transitory computer-readable medium configured to store instructions for execution on a processor, wherein the instructions include:

presenting a graphical display of a plurality of topographic patterns corresponding to different potential measured corneal topographies of an eye of a patient;

presenting an interface that provides for entry of a plurality of vision corrective parameters for the eye of the patient;

receiving the plurality of entered vision corrective parameters and a selection of one of the plurality of topographic patterns;

storing the plurality of entered vision corrective parameters and the selected topographic pattern;

storing a plurality of nomograms in a nomogram data store, wherein each nomogram specifies intrastromal corneal ring segment (ICRS) implantation surgery parameters, and wherein the ICRS implantation surgery parameters include specification of at least one ICRS;

identifying a nomogram from the nomogram data store based on the selected topographic pattern and the plurality of entered vision corrective parameters; and displaying the ICRS implantation surgery parameters specified by the identified nomogram.

* * * * *